(12) United States Patent
Meehan et al.

(10) Patent No.: US 11,517,228 B2
(45) Date of Patent: *Dec. 6, 2022

(54) SENSOR VERIFICATION THROUGH FORWARD VOLTAGE MEASUREMENTS

(71) Applicant: Covidien LP, Mansfield, MA (US)

(72) Inventors: Christopher J. Meehan, Denver, CO (US); Jacob D. Dove, Lafayette, CO (US)

(73) Assignee: COVIDIEN LP, Mansfield, MA (US)

( * ) Notice: Subject to any disclaimer, the term of this patent is extended or adjusted under 35 U.S.C. 154(b) by 248 days.

This patent is subject to a terminal disclaimer.

(21) Appl. No.: 17/082,944

(22) Filed: Oct. 28, 2020

(65) Prior Publication Data
US 2021/0330223 A1 Oct. 28, 2021

Related U.S. Application Data

(63) Continuation of application No. 16/857,695, filed on Apr. 24, 2020, now Pat. No. 10,849,538.

(51) Int. Cl.
*A61B 5/1455* (2006.01)
*A61B 5/1495* (2006.01)
*G01R 19/00* (2006.01)

(52) U.S. Cl.
CPC ........ *A61B 5/14552* (2013.01); *A61B 5/1495* (2013.01); *G01R 19/0084* (2013.01); *A61B 2560/0266* (2013.01); *A61B 2562/0238* (2013.01)

(58) Field of Classification Search
CPC .............. A61B 5/1455; A61B 5/14551; A61B 5/14552; A61B 5/1495; A61B 2560/0266; A61B 2562/0238
See application file for complete search history.

(56) References Cited

U.S. PATENT DOCUMENTS

| | | | |
|---|---|---|---|
| 5,522,389 | A | 6/1996 | Fischer et al. |
| 6,356,774 | B1 | 3/2002 | Bernstein et al. |
| 7,120,480 | B2 | 10/2006 | Chew et al. |
| 8,515,514 | B2 | 8/2013 | Huiku |
| 9,157,773 | B2 | 10/2015 | Joensuu |
| 9,253,852 | B2 | 2/2016 | Campbell et al. |
| 9,404,961 | B2 | 8/2016 | Gonopolskiy et al. |
| 9,651,632 | B1 | 5/2017 | Knapp et al. |
| 9,839,381 | B1 | 12/2017 | Weber et al. |
| 9,861,317 | B2 | 1/2018 | Ochs |
| 10,123,726 | B2 | 11/2018 | Al-Ali et al. |

(Continued)

OTHER PUBLICATIONS

Prosecution History from U.S. Appl. No. 16/857,695, dated May 4, 2020 through Jul. 29, 2020, 10 pp.

(Continued)

*Primary Examiner* — Eric F Winakur
(74) *Attorney, Agent, or Firm* — Shumaker & Sieffert, P.A.

(57) ABSTRACT

A device for measuring oxygen saturation includes circuitry configured to determine a measured difference of forward voltage based on a first forward voltage at a first light emitting diode and a second forward voltage a second light emitting diode and determine that the first and second light emitting diodes are valid based on a calibrated difference of forward voltage and the measured difference of forward voltage. In response to the determination that the first and second light emitting diodes are valid, the circuitry is configured to determine an oxygen saturation level.

20 Claims, 6 Drawing Sheets

(56) References Cited

U.S. PATENT DOCUMENTS

| | | |
|---|---|---|
| 10,849,538 B1 | 12/2020 | Meehan et al. |
| 10,852,230 B1 | 12/2020 | Meehan |
| 2005/0187450 A1 | 8/2005 | Chew et al. |
| 2010/0145645 A1 | 6/2010 | Gonopolskiy et al. |
| 2014/0275890 A1 | 9/2014 | Meehan et al. |
| 2016/0354017 A1 | 12/2016 | Meehan et al. |
| 2018/0235525 A1 | 8/2018 | Blanken |
| 2018/0344227 A1 | 12/2018 | Cronin et al. |
| 2018/0353111 A1 | 12/2018 | Buxton et al. |
| 2020/0138349 A1 | 5/2020 | Lamminmaki et al. |

OTHER PUBLICATIONS

U.S. Appl. No. 17/082,958, filed Oct. 28, 2020, naming inventor Meehan.

International Search Report and Written Opinion of International Application No. PCT/US2021/028688, dated Jun. 28, 2021, 9 pp.

SENSOR VERIFICATION THROUGH FORWARD VOLTAGE MEASUREMENTS

CROSS-REFERENCE TO RELATED APPLICATION

This application is a continuation of U.S. patent application Ser. No. 16/857,695 filed Apr. 24, 2020, which is herein incorporated by reference in its entirety.

TECHNICAL FIELD

This disclosure relates to determining blood oxygen saturation with a physiological monitor, and more particularly, relates to determining regional blood oxygen saturation with a regional oximeter or other medical device.

TECHNICAL FIELD

An oximeter may output small beams of light through blood and measure an absorption of the small beams of light to estimate oxygen saturation levels in the blood. For example, blood with relatively high oxygenated saturation may absorb more light at a particular wavelength than blood with relatively low oxygenated saturation. As such, the oximeter may determine that oxygenated saturation levels in blood increases as less light at the particular wavelength is received after passing through the blood.

SUMMARY

In general, this disclosure relates to devices, systems, and techniques for verification of an oximeter through forward voltage measurements. For example, a device may measure forward voltage at light emitting diodes (LEDs) that are used to measure oxygen saturation. In this example, the device may compare the measured forward voltage at the light emitting diodes to values used during calibration. In this way, the device may be validated to be consistent with calibration values to help to ensure proper construction and/or accuracy of the sensor device.

In one example, a device for measuring oxygen saturation includes: a memory configured to store a calibrated difference of forward voltage; circuitry configured to: apply a first current from an anode of a first light emitting diode to a cathode of the first light emitting diode; while applying the first current, measure a first forward voltage across the anode of the first light emitting diode and the cathode of the first light emitting diode; apply a second current from an anode of a second light emitting diode to a cathode of the second light emitting diode; while applying the second current, measure a second forward voltage across the anode of the second light emitting diode and the cathode of the second light emitting diode; determine a measured difference of forward voltage based on a comparison of the first forward voltage and the second forward voltage; determine that the first light emitting diode and the second light emitting diode are valid based on the calibrated difference of forward voltage and the measured difference of forward voltage; and in response to the determination that the first light emitting diode and the second light emitting diode are valid, determine an oxygen saturation level using the first light emitting diode and the second light emitting diode and output an indication of the oxygen saturation level.

In another example, a method for measuring oxygen saturation includes: applying, by circuitry, a first current from an anode of a first light emitting diode to a cathode of the first light emitting diode; while applying the first current, measuring, by the circuitry, a first forward voltage across the anode of the first light emitting diode and the cathode of the first light emitting diode; applying, by the circuitry, a second current from an anode of a second light emitting diode to a cathode of the second light emitting diode; while applying the second current, measuring, by the circuitry, a second forward voltage across the anode of the second light emitting diode and the cathode of the second light emitting diode; determining, by the circuitry, a measured difference of forward voltage based on a comparison of the first forward voltage and the second forward voltage; determining, by the circuitry, that the first light emitting diode and the second light emitting diode are valid based on a calibrated difference of forward voltage and the measured difference of forward voltage; and in response to determining that the first light emitting diode and the second light emitting diode are valid, determining, by the circuitry, an oxygen saturation level using the first light emitting diode and the second light emitting diode and outputting, by the circuitry, an indication of the oxygen saturation level.

In one example, a system for measuring oxygen saturation includes: a sensor device comprising a first light emitting diode and a second light emitting diode; an oximetry device comprising: a memory configured to store a calibrated difference of forward voltage; circuitry configured to: apply a first current from an anode of the first light emitting diode to a cathode of the first light emitting diode; while applying the first current, measure a first forward voltage across the anode of the first light emitting diode and the cathode of the first light emitting diode; apply a second current from an anode of the second light emitting diode to a cathode of the second light emitting diode; while applying the second current, measure a second forward voltage across the anode of the second light emitting diode and the cathode of the second light emitting diode; determine a measured difference of forward voltage based on a comparison of the first forward voltage and the second forward voltage; determine that the first light emitting diode and the second light emitting diode are valid based on the calibrated difference of forward voltage and the measured difference of forward voltage; and in response to the determination that the first light emitting diode and the second light emitting diode are valid, determine an oxygen saturation level using the first light emitting diode and the second light emitting diode and output an indication of the oxygen saturation level.

DETAILED DESCRIPTION

Figure 1:
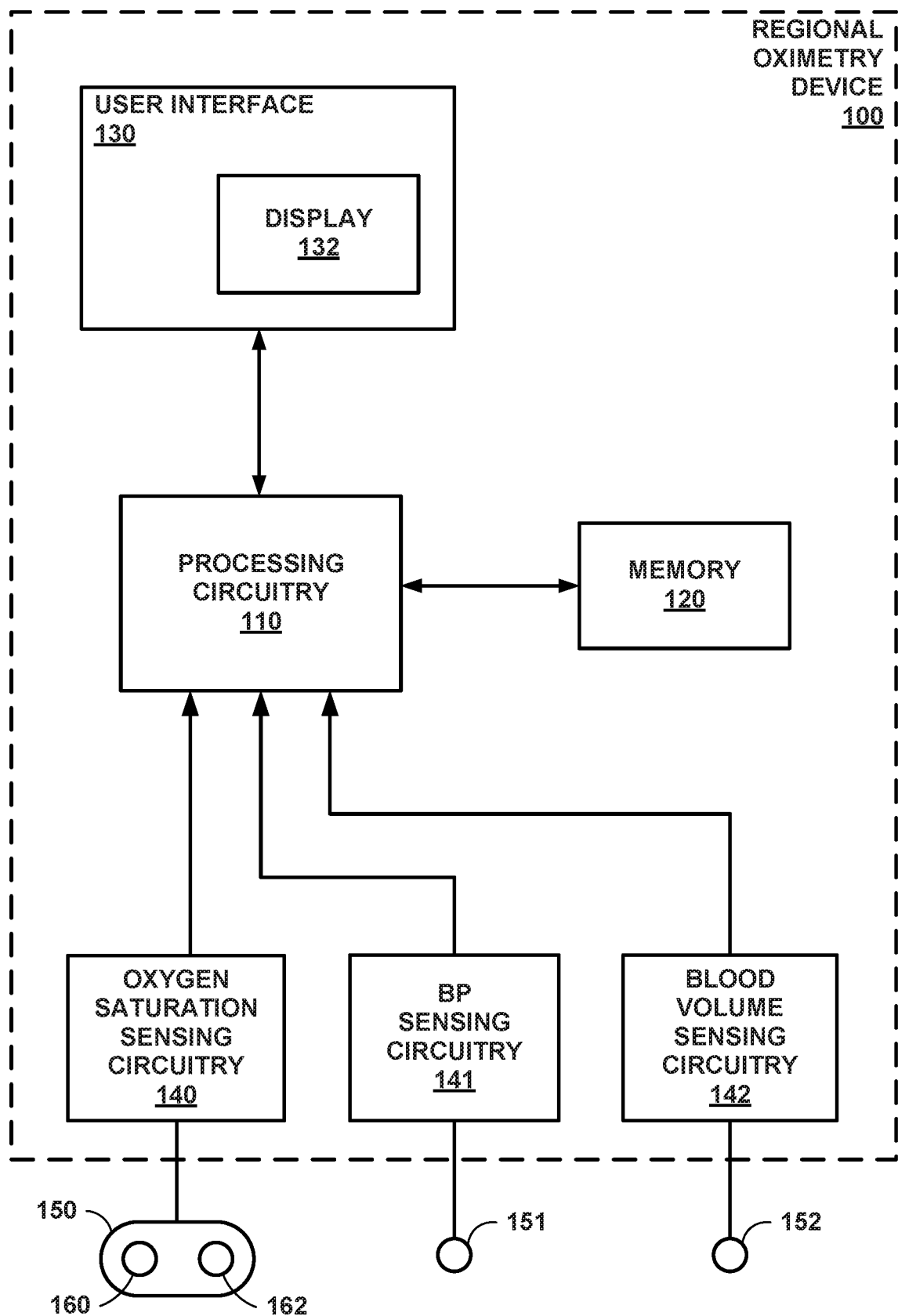
FIG. 1 is a conceptual block diagram illustrating an example regional oximetry device.

An oximeter may refer to a medical device configured to determine an oxygen saturation of an analyzed tissue. For purposes of this disclosure an oximeter may be defined as a device that measures other elements besides oxygenation. For example, an oximeter may measure other characteristics and chemical compositions of blood, like carbon monoxide. In some examples an oximeter may only be used to measure the photoplesmograph of a subject for determination of a pulse rate. Examples of an oximeter may include, for example, a pulse oximeter, a regional oximeter, a CO-Oximeter, or other photometric measurement device. A pulse oximeter may be configured to estimate oxygen saturation of blood. A regional oximeter may be configured to estimate blood oxygen saturation in a region of a subject's (e.g., a human patient) tissue. For example, the regional oximeter may be configured to determine a differential absorption value for each of two or more wavelengths of light received at two different locations on the subject's body to estimate the regional blood oxygen saturation of hemoglobin in a region of the subject's tissue. For each wavelength of light, the regional oximeter may compare the amount of light absorbed by the subject's tissue in a first region to the amount of light absorbed by the subject's tissue in a second region to derive the differential absorption values. A sensor device may include a regional oximeter and a pulse oximeter.

An oximeter (e.g., a pulse oximeter, a regional oximeter, etc.) may include a sensor device that is placed at a site on a patient, for example, on a fingertip, toe, forehead or earlobe, the cerebral cortex, or in the case of a neonate, across a foot, across a hand, or another location. The oximeter may use a light source to pass light through blood perfused tissue and photoelectrically sense the absorption of the light in the tissue. Additional suitable sensor locations may include, for example, a neck to monitor carotid artery pulsatile flow, a wrist to monitor radial artery pulsatile flow, an inside of a patient's thigh to monitor femoral artery pulsatile flow, an ankle to monitor tibial artery pulsatile flow, around or in front of an ear, locations with strong pulsatile arterial flow, or other locations.

The oximeter may be configured to output a photonic signal that interacts with tissue at one or more wavelengths that are attenuated by the blood in an amount representative of the blood constituent concentration. The oximeter may be configured to generate the photonic signal at red and infrared (IR) wavelengths. The oximeter may estimate the blood oxygen saturation of hemoglobin in arterial blood based on an intensity of the photonic signal at the red wavelength and the photonic signal at the infrared wavelength.

Light emitting diodes (LEDs) of an oximeter may be manufactured to output a photonic signal at a particular wavelength with a manufacturing tolerance. For example, a first LED may output a first phonic signal (e.g., red light) at a first wavelength range (e.g., 630 nm-700 nm) with a first manufacturing tolerance of 5%. In this example, a second LED may output a second phonic signal (e.g., infrared light) at a second wavelength range (e.g., 700 nm-1200 nm) with a second manufacturing tolerance of 5%. While various examples described herein refer to a LED that may output relatively low intensity light, in some examples, LEDs may include devices that output relatively intense beams of light of infrared radiation (e.g., laser diodes), vertical-cavity surface-emitting laser, or another device that emits light using at least one p-type junction and at least one n-type junction. Moreover, while examples described herein may refer to a device emitting light (e.g., LED, laser diode, etc.) similar techniques may be used with devices that receive light (e.g., photodiodes).

To account for the manufacturing tolerances, some oximeters may use calibration information that are established for each sensor. For example, some oximeter may be configured to store calibration information about LEDs of the oximeter in memory (e.g., EEPROM). The calibration information may help to account for manufacturing tolerances of the LEDs, which can shift a wavelength of light emitted by the LEDs. However, when an oximeter that is configured for calibration information for a particular set of LEDs is used with LEDs having different manufacturing tolerances, the oximetry may generate incorrect measurement values.

In accordance with the techniques of the disclosure, a device (e.g., an oximeter) may be configured to verify (e.g., validate) that the LEDs used by the device for determining blood oxygen saturation values conform to the stored calibration information (e.g., are within the range defined by the calibration information). The validation of the LEDs to the calibration information indicates that the LEDs are verified to be used for determining oxygen levels (e.g., measurements should be accurate).

In some examples, the device may determine a forward voltage across each of the LEDs as one way to determine that the LEDs used by the device conforms to the calibration information (e.g., is within the range defined by the calibration information). However, there may be deficiencies in relying solely on forward voltage. For example, different cable resistances may significantly change a measured forward voltage across the LED. As such, to account for cable resistance, some examples may use four-terminal sensing where an extra wire is placed at each side of an LED to help to reduce the effects of cable resistance, which adds to complexity and cost of the system.

Rather than always using calibration information to determine blood oxygen saturation values or relying on four-terminal sensing, a device (e.g., oximeter) may use a difference of forward voltages of LEDs to verify that the LEDs used by the device correspond to the calibration information (e.g., satisfy a condition to confirm that the LEDs will provide accurate measurements). During calibration, the device may measure a first forward voltage across the LEDs in response to positive current and a second forward voltage across the LEDs in response to negative current having a same magnitude as the positive current (e.g., device measures the first forward voltage and the second forward voltage using opposite polarity currents having same magnitude). In some examples, the device may perform only a single measurement of the first forward voltage. In some examples, however, the device may perform more than one measurements of the forward voltage each at a different respective current. For instance, the device may measure a first forward voltage for a first current, a first forward voltage for a second current different (e.g., greater than, less than, etc.) the first current, and so forth during calibration. In this example, the device may store a calibrated difference of the first forward voltage and the second forward voltage ("calibrated $\Delta VF$") in memory along with calibration information for the LEDs. After calibration, the device may measure the first forward voltage in response to the positive current and the second forward voltage in response to the negative current and generate a measured difference of the first forward voltage and the second forward voltage ("measured $\Delta VF$"). If the measured $\Delta VF$ and the calibrated $\Delta VF$ are within a certain tolerance, then the device may determine that the LEDs in service at the device (e.g., an oximeter) are consistent with the calibration information and therefore validated. In response to determining that the LEDs in service at the device are valid, the device may determine, based on the calibration information, an oxygen saturation level using the LEDs. If the measured ΔVF and the calibrated ΔVF are not within the certain tolerance, then the device may determine that the LEDs in service at the device are not consistent with the calibration information and therefore that the LEDs in service at the device are not validated. In response to determining that the LEDs in service at the device are not validated, the device may refrain from determining an oxygen saturation level. In this way, the device may be validated to be consistent with calibration values to help to ensure proper construction and accuracy of the device.

In some examples, a device (e.g., an oximeter) may use the measured ΔVF to detect LED temperature. The device may match the measured ΔVF with a ΔVF stored in a particular table entry. The device may determine that the temperature at the LED corresponds to a temperature in the particular table entry. In some examples, the device may encrypt and decrypt information (e.g., calibration information) in memory using ΔVF as an encryption key.

FIG. 1 is a conceptual block diagram illustrating an example regional oximetry device 100. While the example of FIG. 1 describes a regional oximetry device, techniques described herein for validating light emitting diodes may be used in other devices, such as, for example, a pulse oximetry device, a co-oximeter device, or another oximeter device. Regional oximetry device 100 includes processing circuitry 110, memory 120, user interface 130, display 132, sensing circuitry 140, 141, and 142, and sensing device(s) 150, 151, and 152. In some examples, regional oximetry device 100 may be configured to determine and display the cerebral autoregulation status of a patient, e.g., during a medical procedure or for more long-term monitoring, such as monitoring of prenatal infants, children, or adults. A clinician may receive information regarding the cerebral autoregulation status of a patient via display 132 and adjust treatment or therapy to the patient based on the cerebral autoregulation status information. Although regional oximetry device 100 is described as an example device herein, other devices may calculate blood pressure and/or use blood pressure for other physiological monitoring and perform similar a compensation process on blood pressures subjected to abrupt changes in the measured blood pressure values.

Processing circuitry 110 as well as other processors, processing circuitry, controllers, control circuitry, and the like, described herein, may include one or more processors. Processing circuitry 110 may include any combination of integrated circuitry, discrete logic circuity, analog circuitry, such as one or more microprocessors, digital signal processors (DSPs), application specific integrated circuits (ASICs), or field-programmable gate arrays (FPGAs). In some examples, processing circuitry 110 may include multiple components, such as any combination of one or more microprocessors, one or more DSPs, one or more ASICs, or one or more FPGAs, as well as other discrete or integrated logic circuitry, and/or analog circuitry.

Memory 120 may be configured to store measurements of blood pressure, oxygen saturation, blood volume, other physiological parameters, relationships between blood pressure and physiological parameters, MAP values, rSO2 values, COx values, BVS values, HVx values, and/or value(s) of an limit of autoregulation (LLA) and/or a upper limit of autoregulation (ULA), for example. Memory 120 may also be configured to store data such as thresholds for detecting abrupt changes in blood pressure, previous LLA and ULA values, and/or other physiological parameters and expected values of physiological parameters. Memory 120 may also be configured to store data such as threshold levels for physiological parameters, threshold values for blood pressure, and/or threshold levels for signal quality metrics. The thresholds or other data may stay constant throughout the use of device 100 and across multiple patients, or these values may change over time. Memory 120 may store a calibrated difference of forward voltage for validating sensing device 150.

Memory 120 may store program instructions, which may include one or more program modules, which are executable by processing circuitry 110. When executed by processing circuitry 110, such program instructions may cause processing circuitry 110 to provide the functionality ascribed to it herein. For example, memory 120 may store instructions regarding how to determine abrupt changes in measured blood pressure, calculating ULA and LLA values, and presenting information to the user via user interface 130. The program instructions may be embodied in software, firmware, and/or RAMware. Memory 120, as well as other memory devices described herein (e.g., memory 220 shown in FIG. 2), may include any volatile, non-volatile, magnetic, optical, circuitry, or electrical media, such as a random access memory (RAM), read-only memory (ROM), non-volatile RAM (NVRAM), electrically-erasable programmable ROM (EEPROM), flash memory, or any other digital media.

User interface 130 and/or display 132 may be configured to present information to a user (e.g., a clinician). User interface 130 and/or display 132 may be configured to present a graphical user interface to a user, where each graphical user interface may include indications of values of one or more physiological parameters of a subject. For example, processing circuitry 110 may be configured to present blood pressure values, other physiological parameter values (e.g., heart rate), and indications of cerebral autoregulation status of a patient via display 132. In some examples, if processing circuitry 110 determines that the cerebral autoregulation status of the patient is impaired, then processing circuitry 110 may present a notification (e.g., an alert) indicating the impaired cerebral autoregulation status via display 132. As another example, processing circuitry 110 may present, via display 132, estimates of regional oxygen saturation (rSO2) for a patient, an estimate of the blood oxygen saturation (SpO2) determined by processing circuitry 110, pulse rate information, respiration rate information, blood pressure, any other patient parameters, or any combination thereof.

User interface 130 and/or display 132 may include a monitor, cathode ray tube display, a flat panel display such as a liquid crystal (LCD) display, a plasma display, or a light emitting diode (LED) display, personal digital assistant, mobile phone, tablet computer, laptop computer, any other suitable display device, or any combination thereof. User interface 130 may also include means for projecting audio to a user, such as speaker(s). Processing circuitry 110 may be configured to present, via user interface 130, a visual, audible, or somatosensory notification (e.g., an alarm signal) indicative of the patient's autoregulation status. User interface 130 may include or be part of any suitable device for conveying such information, including a computer workstation, a server, a desktop, a notebook, a laptop, a handheld computer, a mobile device, or the like. In some examples, processing circuitry 110 and user interface 130 may be part of the same device or supported within one housing (e.g., a computer or monitor).

Sensing circuitry 140, 141, and 142 may be configured to receive physiological signals sensed by respective sensing device(s) 150, 151, and 152 and communicate the physiological signals to processing circuitry 110. Sensing device(s) 150, 151, and 152 may include any sensing hardware configured to sense a physiological parameter of a patient, such as, but not limited to, one or more electrodes, optical receivers, blood pressure cuffs, or the like. Sensing circuitry 140, 141, and 142 may convert the physiological signals to usable signals for processing circuitry 110, such that processing circuitry 110 is configured to receive signals generated by sensing circuitry 140, 141, and 142. Sensing circuitry 140, 141, and 142 may receive signals indicating physiological parameters from a patient, such as, but not limited to, blood pressure, regional oxygen saturation, heart rate, and respiration. Sensing circuitry 140, 141, and 142 may include, but are not limited to, blood pressure sensing circuitry, oxygen saturation sensing circuitry, heart rate sensing circuitry, temperature sensing circuitry, electrocardiography (ECG) sensing circuitry, electroencephalogram (EEG) sensing circuitry, or any combination thereof. In some examples, sensing circuitry 140, 141, and 142 and/or processing circuitry 110 may include signal processing circuitry such as an analog-to-digital converter.

Oxygen saturation sensing device 150 is a regional oxygen saturation sensor configured to generate an oxygen saturation signal indicative of blood oxygen saturation within the venous, arterial, and/or capillary systems within a region of the patient. For example, oxygen saturation sensing device 150 may be configured to be placed on the patient's forehead and may be used to determine the oxygen saturation of the patient's blood within the venous, arterial, and/or capillary systems of a region underlying the patient's forehead (e.g., in the cerebral cortex).

Oxygen saturation sensing device 150 may include emitter 160 and detector 162. Emitter 160 may include at least two light emitting diodes (LEDs), each configured to emit at different wavelengths of light, e.g., red and near infrared light. In some examples, light drive circuitry (e.g., within sensing device 150, sensing circuitry 140, and/or processing circuitry 110) may provide a light drive signal to drive emitter 160 and to cause emitter 160 to emit light. In some examples, the LEDs of emitter 160 emit light in the wavelength range of about 600 nanometers (nm) to about 1000 nm. In a particular example, one LED of emitter 160 is configured to emit light at a wavelength of about 730 nm and the other LED of emitter 160 is configured to emit light at a wavelength of about 810 nm. Other wavelengths of light may also be used in other examples.

Detector 162 may include a first detection element positioned relatively "close" (e.g., proximal) to emitter 160 and a second detection element positioned relatively "far" (e.g., distal) from emitter 160 (these multiple detectors are shown as a single detector in the example of FIG. 1). Light intensity of multiple wavelengths may be received at both the "close" and the "far" detector 162. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation signal for the target tissues over time. Oxygen saturation sensing device 150 may provide the regional oxygen saturation signal to processing circuitry 110 or to any other suitable processing device to enable evaluation of the patient's autoregulation status.

Blood pressure sensing device 151 and oxygen saturation sensing device 150 may each be placed on the same or different parts of the patient's body. For example, blood pressure sensing device 151 and oxygen saturation sensing device 150 may be physically separate from each other and separately placed on the patient. As another example, blood pressure sensing device 151 and oxygen saturation sensing device 150 may in some cases be part of the same sensor or supported by a single sensor housing. For example, blood pressure sensing device 151 and oxygen saturation sensing device 150 may be part of an integrated oximetry system configured to non-invasively measure blood pressure (e.g., based on time delays in a PPG signal) and regional oxygen saturation. One or both of blood pressure sensing device 151 or oxygen saturation sensing device 150 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an example regional oximetry device 100 is shown in FIG. 1, the components illustrated in FIG. 1 are not intended to be limiting. Additional or alternative components and/or implementations may be used in other examples.

Blood pressure sensing device 151 may be any sensor or device configured to obtain the patient's blood pressure (e.g., arterial blood pressure). In one example, the blood pressure sensing device 151 may include or be connected to a probe configured to be inserted into a blood pressure of the patient. In another example, blood pressure sensing device 151 may include a blood pressure cuff for non-invasively monitoring blood pressure or an arterial line for invasively monitoring blood pressure (e.g., a pressure probe configured to be placed within an artery or vein). In certain examples, blood pressure sensing device 151 may include one or more pulse oximetry sensors. In some such cases, the patient's blood pressure may be derived by processing time delays between two or more characteristic points within a single plethysmography (PPG) signal obtained from a single pulse oximetry sensor.

Processing circuitry 110 may be configured to receive one or more physiological signals generated by sensing devices 150, 151, and 152 and sensing circuitry 140, 141, and 142. The physiological signals may include a signal indicating blood pressure, a signal indicating oxygen saturation, and/or a signal indicating blood volume of a patient. Processing circuitry 110 may be configured to determine a relationship between blood pressure values of the patient and a physiological parameter of the patient, such as a correlation index (e.g., COx, a hemoglobin volume index (HVx)), an oxygen saturation value, a blood volume value, a gradient-based metric of two or more physiological parameters, and/or another physiological parameter. Processing circuitry 110 can determine a gradients-based metric by determining respective gradients of signals for physiological parameters and determining whether the respective gradients trend together.

Processing circuitry 110 may be configured to determine the blood pressure values for which the physiological parameter is less than or greater than one or more threshold values. As an example, processing circuitry 110 may determine an estimate of the lower limit of cerebral autoregulation (LLA) based on the lowest blood pressure value at which the expected value of COx is less than a threshold value, such as 0.5, 0.4, 0.3, 0.2, 0.1, or 0.0 (e.g., wherein 1.0 represents full correlation and 0.0 represents no correlation between blood pressure and rSO2). Thus, processing circuitry 110 may determine estimates of the limits of cerebral autoregulation (e.g., the LLA and the ULA) based on the blood pressure and rSO2. Regional oximetry device 100 may omit blood pressure and/or blood volume circuitry. For example, regional oximetry device 100 may omit sensing circuitry 141 and/or sensing device 151. In some examples, regional oximetry device 100 may omit sensing circuitry 142 and sensing device 152. In some examples, regional oximetry device 100 may include only circuitry for determining an oxygen saturation level.

In accordance with the techniques of the disclosure, a device such as regional oximetry device 100 may include memory circuitry (e.g., memory 120) configured to store a calibrated difference of forward voltage. Device 100 may also include processing circuitry (e.g., processing circuitry 110) that is configured to apply a first current from an anode of a first light emitting diode (e.g., first LED of emitter 160) to a cathode of the first light emitting diode. For example, light drive circuitry (e.g., within sensing device 150, sensing circuitry 140, and/or processing circuitry 110) may apply the first current (e.g., a positive current) to emitter 160 to cause the first current to flow through a first light emitting diode (e.g., a light emitting diode for emitting red light). While applying the first current, voltage measuring circuitry (e.g., within sensing device 150, sensing circuitry 140, and/or processing circuitry 110) may measure a first forward voltage across the anode of the first light emitting diode and the cathode of the first light emitting diode. For example, light drive circuitry (e.g., within sensing device 150, sensing circuitry 140, and/or processing circuitry 110) may measure an indication of voltage output at terminals of a source supplying the first current while applying the first current.

Light drive circuitry (e.g., within sensing device 150, sensing circuitry 140, and/or processing circuitry 110) may apply a second current from an anode of a second light emitting diode (e.g., second LED of emitter 160) to a cathode of the second light emitting diode. For example, light drive circuitry (e.g., within sensing device 150, sensing circuitry 140, and/or processing circuitry 110) may apply a second current (e.g., a negative current) to emitter 160 to cause the second current to flow through the second light emitting diode (e.g., a light emitting diode for emitting infrared light). While applying the second current, voltage measuring circuitry (e.g., within sensing device 150, sensing circuitry 140, and/or processing circuitry 110) may be configured to measure a second forward voltage across the anode of the second light emitting diode and the cathode of the second light emitting diode. For example, light drive circuitry (e.g., within sensing device 150, sensing circuitry 140, and/or processing circuitry 110) may measure an indication of voltage output at terminals of a source supplying the second current.

Processing circuitry 110 may be configured to determine a measured difference of forward voltage based on a comparison of the first forward voltage and the second forward voltage. For example, processing circuitry 110 may subtract an absolute value of the first forward voltage and an absolute value of the second forward voltage to generate the measured difference of forward voltage. Processing circuitry 110 may be configured to determine that the first light emitting diode and the second light emitting diode are valid based on the calibrated difference of forward voltage and the measured difference of forward voltage. For example, processing circuitry 110 may determine that the first light emitting diode and the second light emitting diode are valid in response to determining that a difference between the calibrated difference of forward voltage and the measured difference of forward voltage is less than a threshold value. The threshold value may be a user configurable value.

Processing circuitry 110 may be configured to determine an oxygen saturation level using the first light emitting diode and the second light emitting diode in response to the determination that the first light emitting diode and the second light emitting diode are valid. For example, processing circuitry 110 may determine an oxygen saturation in tissue of a subject only in response to determining that first light emitting diode and the second light emitting diode are valid. Processing circuitry 110 may refrain form determining an oxygen saturation in tissue of a subject in response to determining that first light emitting diode and the second light emitting diode are not validated. For example, in response to determining that first light emitting diode and the second light emitting diode are not validated, processing circuitry 110 may output an error code on display 132.

In the above examples, processing circuitry 110, light drive circuitry, and voltage measuring circuitry are described as performing the example techniques, wherein light drive circuitry and voltage measurement circuitry may be part of processing circuitry 110, sensing device 150 and/or sensing circuitry 140). However, any one or combination of processing circuitry 110, sensing circuitry 140, and/or sensing device 150 may be configured to perform the example techniques. For instance, the example techniques may be performed by circuitry, and example of the circuitry includes any one or any combination of processing circuitry 110, sensing circuitry 140, and/or sensing device 150.

Figure 2:
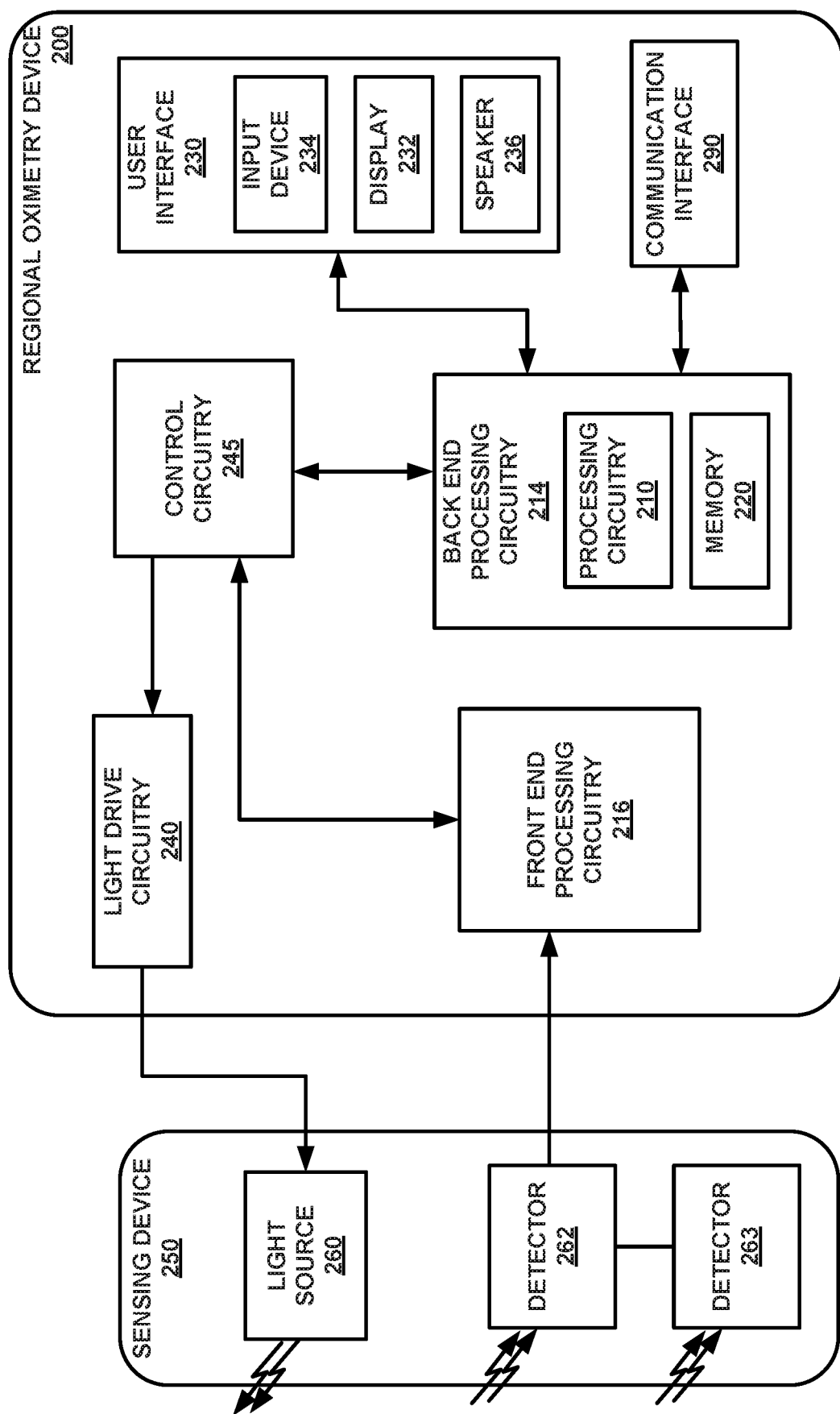
FIG. 2 is a conceptual block diagram illustrating an example regional oximetry device configured to monitor an autoregulation status of a patient.

FIG. 2 is a conceptual block diagram illustrating an example regional oximetry device 200 configured to monitor the autoregulation status of a patient. While the example of FIG. 2 describes a regional oximetry device, techniques described herein for validating light emitting diodes may be used in other devices, such as, for example, a pulse oximetry device. In the example shown in FIG. 2, regional oximetry device 200 is coupled to sensing device 250 and may be collectively referred to as a regional oximetry system, which each generate and process physiological signals of a subject. Regional oximetry device 200 and sensing device 250 may be examples of regional oximetry device 100 and sensing device 150, respectively, of FIG. 1. In some examples, sensing device 250 and regional oximetry device 200 may be part of an oximeter. As shown in FIG. 2, regional oximetry device 200 includes back-end processing circuitry 214, user interface 230, light drive circuitry 240, front-end processing circuitry 216, control circuitry 245, and communication interface 290. Regional oximetry device 200 may be communicatively coupled to sensing device 250. Regional oximetry device 200 is an example of regional oximetry device 100 shown in FIG. 1. In some examples, regional oximetry device 200 may also include a blood pressure sensor and/or a blood volume sensor (e.g., sensing devices 151 and 152 of FIG. 1).

In the example shown in FIG. 2, sensing device 250 includes light source 260, detector 262, and detector 263. Light source 260 may be an example of light source 160 of FIG. 1. Detectors 262 and 263 may be examples of detector 162 of FIG. 1. In some examples, sensing device 250 may include more than two detectors. Light source 260 may be configured to emit photonic signals having two or more wavelengths (e.g., up to four or more wavelengths, more than 4 wavelengths, etc.) of light (e.g., red and infrared (IR), or another wavelength of light) into a subject's tissue. For example, light source 260 may include a red light emitting light source and an IR light emitting light source, (e.g., red and IR LEDs), for emitting light into the tissue of a subject to generate physiological signals. In some examples, the red wavelength may be between about 600 nm and about 700 nm, and the IR wavelength may be between about 800 nm and about 1000 nm. Other wavelengths of light may be used in other examples. Light source 260 may include any number of light sources with any suitable characteristics. In examples in which an array of sensors is used in place of sensing device 250, each sensing device may be configured to emit a single wavelength. For example, a first sensing device may emit only a red light while a second sensing device may emit only an IR light. In some examples, light source 260 may be configured to emit two or more wavelengths of near-infrared light (e.g., wavelengths between 600 nm and 1000 nm) into a subject's tissue. In some examples, light source 260 may be configured to emit four wavelengths of light (e.g., 724 nm, 770 nm, 810 nm, and 850 nm) into a subject's tissue. In some examples, the subject may be a medical patient.

As used herein, the term "light" may refer to energy produced by radiative sources and may include one or more of ultrasound, radio, microwave, millimeter wave, infrared, visible, ultraviolet, gamma ray or X-ray electromagnetic radiation. Light may also include any wavelength within the radio, microwave, infrared, visible, ultraviolet, or X-ray spectra, and that any suitable wavelength of electromagnetic radiation may be appropriate for use with the present techniques. Detectors 262 and 263 may be chosen to be specifically sensitive to the chosen targeted energy spectrum of light source 260.

Detectors 262 and 263 may be configured to detect the intensity of multiple wavelengths of near-infrared light. In some examples, detectors 262 and 263 may be configured to detect the intensity of light at the red and IR wavelengths. In some examples, an array of detectors may be used and each detector in the array may be configured to detect an intensity of a single wavelength. In operation, light may enter detector 262 after passing through the subject's tissue, including skin, bone, and other shallow tissue (e.g., non-cerebral tissue and shallow cerebral tissue). Light may enter detector 263 after passing through the subject's tissue, including skin, bone, other shallow tissue (e.g., non-cerebral tissue and shallow cerebral tissue), and deep tissue (e.g., deep cerebral tissue). Detectors 262 and 263 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detectors 262 and 263.

For example, detectors 262 and/or detector 263 may determine a first intensity of a first received photonic signal corresponding to a first output photonic signal (e.g., red light) output using a first light emitting diode of light source 260. More specifically, processing circuitry (e.g., light drive circuitry 240) may be configured to drive the first light emitting diode of light source 260 to output the first output photonic signal towards a subject's tissue and receive, from detector 262 and/or detector 263, the first received photonic signal after the first output photonic signal transmits through the subject's tissue. Similarly, detectors 262 and/or detector 263 may determine a second intensity of a second received photonic signal corresponding to a second output photonic signal (e.g., infrared light) output using the second light emitting diode. More specifically, processing circuitry (e.g., light drive circuitry 240) may be configured to drive a second light emitting diode of light source 260 to output the second output photonic signal towards the subject's tissue and receive, from detector 262 and/or detector 263, the second received photonic signal after the second output photonic signal transmits through the subject's tissue.

After converting the received light to an electrical signal, detectors 262 and 263 may send the detection signals to regional oximetry device 200, which may process the detection signals and determine physiological parameters (e.g., based on the absorption of the red and IR wavelengths in the subject's tissue at both detectors). For example, regional oximetry device 200 may determine an oxygen saturation level based on the first intensity of the first received photonic signal and the second intensity of the second received photonic signal. More specifically, processing circuitry 210 may estimate a first wavelength for the first output photonic signal based on calibration information stored in memory 220. For instance, processing circuitry 210 may estimate the first wavelength for the first output photonic signal as equal to a first wavelength identified in the calibration information stored in memory 220. In some instances, processing circuitry 210 may estimate the first wavelength for the first output photonic signal as equal to a first wavelength identified in the calibration information stored in memory 220 that corresponds to an estimated operating temperature at light source 260 (e.g., the first light emitting diode).

Similarly, processing circuitry 210 may estimate a second wavelength for the second output photonic signal output based on calibration information stored in memory 220. For instance, processing circuitry 210 may estimate the second wavelength for the second output photonic signal as equal to a second wavelength identified in the calibration information stored in memory 220. In some instances, processing circuitry 210 may estimate the second wavelength for the second output photonic signal as equal to a second wavelength identified in the calibration information stored in memory 220 that corresponds to an estimated operating temperature at light source 260 (e.g., the second light emitting diode).

In this example, processing circuitry 210 may determine the oxygen saturation level is based on the first wavelength for the first output photonic signal and the second wavelength for the second output photonic signal. For instance, processing circuitry 210 may determine the oxygen saturation level by matching an amount of absorption of the first wavelength (e.g., a difference in magnitude between an emitted light and a received light) and matching an amount of absorption of the second wavelength in a table and outputting a corresponding oxygen saturation level for the absorption of the first wavelength and the absorption of the second wavelength.

Processing circuitry 210 may output an indication of the oxygen saturation level. For example, processing circuitry 210 may store an indication of the oxygen saturation level (e.g., a numerical value indicating the oxygen saturation level) for storage at memory 220. Processing circuitry 210 may output an indication of the oxygen saturation level (e.g., a numerical value indicating the oxygen saturation level) to user interface 230 for output on display 232. Processing circuitry 210 may output an indication of the oxygen saturation level (e.g., a numerical value indicating the oxygen saturation level) to communication interface 290 for storage and/or output at one or more external or implanted devices.

Processing circuitry 210 may be decrypt calibration information stored in memory 220. For example, processing circuitry 210 may encrypt the calibration information stored in memory 220 using a measured difference of forward voltage as an encryption key. As such, processing circuitry 210 may decrypt the encrypted calibration information using a measured difference of forward voltage as a key. In this way, processing circuitry 210 may help to ensure that calibration information stored in memory 220 is used in a safe manner.

In some examples, one or more of the detection signals may be preprocessed by sensing device 250 before being transmitted to regional oximetry device 200. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation," the entire content of which is incorporated herein by reference.

Control circuitry 245 may be coupled to light drive circuitry 240, front-end processing circuitry 216, and back-end processing circuitry 214, and may be configured to control the operation of these components. In some examples, control circuitry 245 may be configured to provide timing control signals to coordinate their operation. For example, light drive circuitry 240 may generate one or more light drive signals, which may be used to turn on and off light source 260, based on the timing control signals provided by control circuitry 245. Front-end processing circuitry 216 may use the timing control signals to operate synchronously with light drive circuitry 240. For example, front-end processing circuitry 216 may synchronize the operation of an analog-to-digital converter and a demultiplexer with the light drive signal based on the timing control signals. In addition, the back-end processing circuitry 214 may use the timing control signals to coordinate its operation with front-end processing circuitry 216.

Light drive circuitry 240, as discussed above, may be configured to generate a light drive signal that is provided to light source 260 of sensing device 250. The light drive signal may, for example, control the intensity of light source 260 and the timing of when light source 260 is turned on and off. In some examples, light drive circuitry 240 provides one or more light drive signals to light source 260. Where light source 260 is configured to emit two or more wavelengths of light, the light drive signal may be configured to control the operation of each wavelength of light. The light drive signal may comprise a single signal or may comprise multiple signals (e.g., one signal for each wavelength of light).

Front-end processing circuitry 216 may perform any suitable analog conditioning of the detector signals. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. The conditioned analog signals may be processed by an analog-to-digital converter of circuitry 216, which may convert the conditioned analog signals into digital signals. Front-end processing circuitry 216 may operate on the analog or digital form of the detector signals to separate out different components of the signals. Front-end processing circuitry 216 may also perform any suitable digital conditioning of the detector signals, such as low pass, high pass, band pass, notch, averaging, or any other suitable filtering, amplifying, performing an operation on the signal, performing any other suitable digital conditioning, or any combination thereof. Front-end processing circuitry 216 may decrease the number of samples in the digital detector signals. In some examples, front-end processing circuitry 216 may also remove dark or ambient contributions to the received signal.

Back-end processing circuitry 214 may include processing circuitry 210 and memory 220. Processing circuitry 210 may include an assembly of analog or digital electronic components and may be configured to execute software, which may include an operating system and one or more applications, as part of performing the functions described herein with respect to, e.g., processing circuitry 110 of FIG. 1. Processing circuitry 210 may receive and further process physiological signals received from front-end processing circuitry 216. For example, processing circuitry 210 may determine one or more physiological parameter values based on the received physiological signals. For example, processing circuitry 210 may compute one or more of regional oxygen saturation, blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof.

Processing circuitry 210 may perform any suitable signal processing of a signal, such as any suitable band-pass filtering, adaptive filtering, closed-loop filtering, any other suitable filtering, and/or any combination thereof. Processing circuitry 210 may also receive input signals from additional sources not shown. For example, processing circuitry 210 may receive an input signal containing information about treatments provided to the subject from user interface 230. Additional input signals may be used by processing circuitry 210 in any of the determinations or operations it performs in accordance with back-end processing circuitry 214 or regional oximetry device 200.

Processing circuitry 210 is an example of processing circuitry 110 and is configured to perform the techniques of this disclosure. For example, processing circuitry 210 may be configured to determine a measured difference of forward voltage based on a comparison of a first forward voltage of a first light emitting diode of light source 260 and the second forward voltage of a second light emitting diode of light source 260. For example, processing circuitry 210 may subtract an absolute value of the first forward voltage and an absolute value of the second forward voltage to generate the measured difference of forward voltage. Processing circuitry 210 may be configured to determine that the first light emitting diode and the second light emitting diode of light source 260 are valid based on the calibrated difference of forward voltage and the measured difference of forward voltage. For example, processing circuitry 210 may determine that the first light emitting diode and the second light emitting diode of light source 260 are valid in response to determining that a difference between the calibrated difference of forward voltage and the measured difference of forward voltage is less than a predetermined threshold. Processing circuitry 210 may be configured to determine an oxygen saturation level using the first light emitting diode and the second light emitting diode of light source 260 in response to the determination that the first light emitting diode and the second light emitting diode are valid.

Memory 220 may include any suitable computer-readable media capable of storing information that can be interpreted by processing circuitry 210. In some examples, memory 220 may store reference absorption curves, reference sets, determined values, such as blood oxygen saturation, pulse rate, blood pressure, fiducial point locations or characteristics, initialization parameters, any other determined values, or any combination thereof, in a memory device for later retrieval. Memory 220 may also store thresholds for detecting abrupt changes in blood pressure, and so on. Back-end processing circuitry 214 may be communicatively coupled with user interface 230 and communication interface 290.

Memory 220 may store a calibrated difference of forward voltage for light emitting diodes of light source 260. For example, during a calibration of sensing device 250, device 200 (e.g., one or more of light drive circuitry 240, front end processing circuitry 216, back end processing circuitry 214, etc.) may generate the calibrated difference of forward voltage for light emitting diodes of light source 260. For instance, device 200 may determine, during calibration of sensing device 250, a calibrated difference of forward voltage based on a comparison of a first forward voltage of a first light emitting diode of light source 260 and the second forward voltage of a second light emitting diode of light source 260. For example, processing circuitry 210 may subtract an absolute value of the first forward voltage during calibration of sensing device 250 and an absolute value of the second forward voltage during calibration of sensing device 250 to generate the calibrated difference of forward voltage.

During calibration of sensing device 250, device 200 or another device (e.g., a calibration device) may generate calibration information. For example, device 200 or a calibration device may generate an indication of a first wavelength output by a first light emitting diode of light source 260 and an indication of a second wavelength output by a second light emitting diode of light source 260. Memory 220 may store the calibration information based on the indication of a first wavelength output by a first light emitting diode of light source 260 and an indication of a second wavelength output by a second light emitting diode of light source 260. In some examples, device 200 may encrypt the calibration information. As used herein, calibration information may include information for accounting for manufacturing tolerances of light source 260, such as, for example, but not limited to, a wavelength output by light emitting diodes of light source 260. For example, device 200 may encrypt the calibration information based on the calibrated difference of forward voltage. For instance, device 200 may encrypt the calibration information using the calibrated difference of forward voltage as an encryption key.

User interface 230 may include input device 234, display 232, and speaker 236 in some examples. User interface 230 is an example of user interface 130 shown in FIG. 1, and display 232 is an example of display 132 shown in FIG. 1. User interface 230 may include, for example, any suitable device such as one or more medical devices (e.g., a medical monitor that displays various physiological parameters, a medical alarm, or any other suitable medical device that either displays physiological parameters or uses the output of back-end processing 214 as an input), one or more display devices (e.g., monitor, personal digital assistant (PDA), mobile phone, tablet computer, clinician workstation, any other suitable display device, or any combination thereof), one or more audio devices, one or more memory devices, one or more printing devices, any other suitable output device, or any combination thereof.

Input device 234 may include one or more of any type of user input device such as a keyboard, a mouse, a touch screen, buttons, switches, a microphone, a joystick, a touch pad, or any other suitable input device or combination of input devices. In other examples, input device 234 may be a pressure-sensitive or presence-sensitive display that is included as part of display 232. Input device 234 may also receive inputs to select a model number of sensing device 250, blood pressure sensor 250 (FIG. 2), or blood pressure processing equipment. In some examples, processing circuitry 210 may determine the type of presentation for display 232 based on user inputs received by input device 234.

Figure 3:
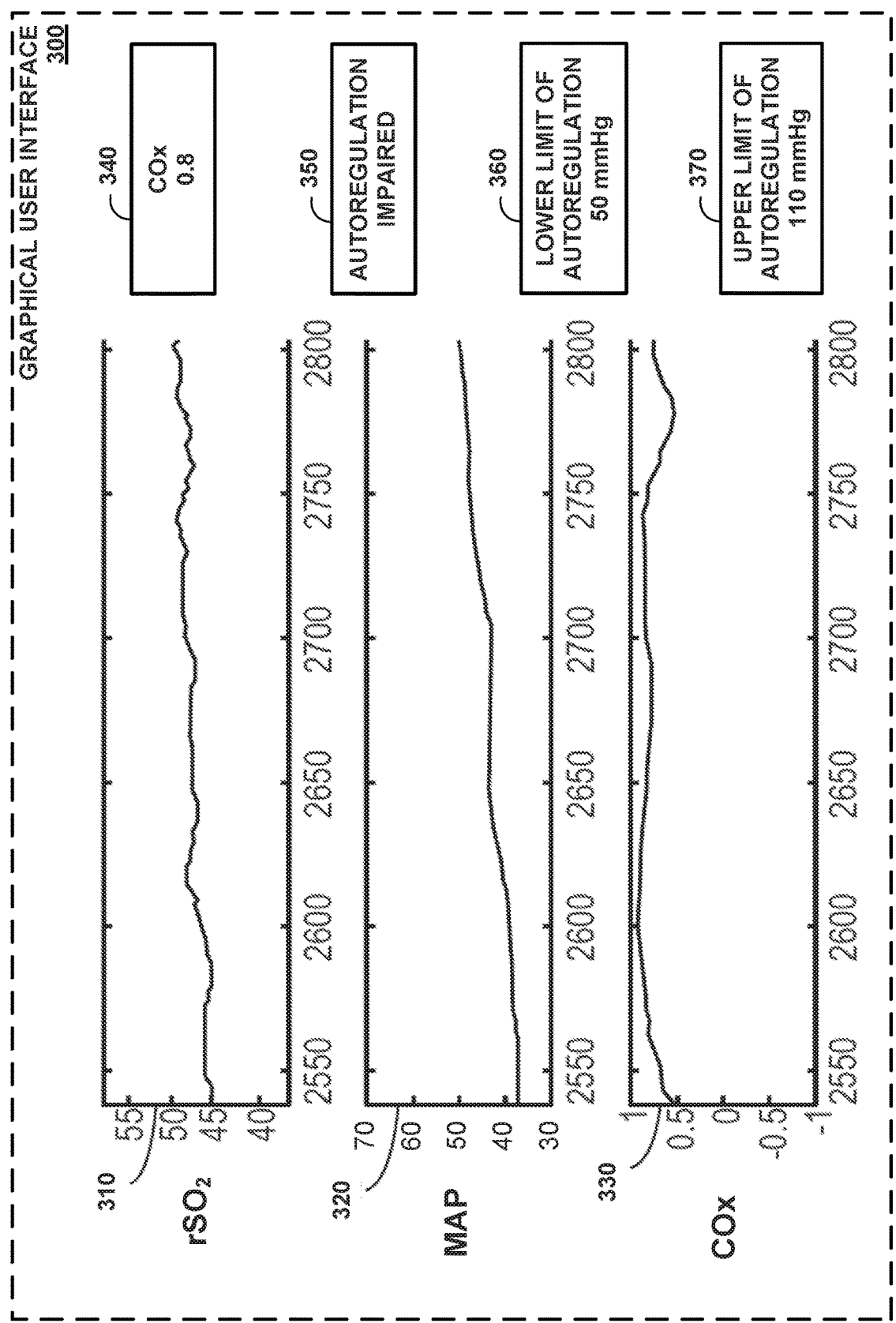
FIG. 3 is a conceptual diagram illustrating an example graphical user interface including autoregulation information presented on a display.

In some examples, the subject may be a medical patient and display 232 may exhibit a list of values which may generally apply to the subject, such as, for example, an oxygen saturation signal indicator, a blood pressure signal indicator, a COx signal indicator, a COx value indicator, and/or an autoregulation status indicator. Display 232 may also be configured to present additional physiological parameter information. Graphical user interface 300 shown in FIG. 3 is an example of an interface that can be presented via display 232 of FIG. 2 under the control of processing circuitry 210. Additionally, display 232 may present, for example, one or more estimates of a subject's regional oxygen saturation generated by regional oximetry device 200 (referred to as an "rSO2" measurement). Display 232 may also present indications of the upper and lower limits of cerebral autoregulation. In some examples, user interface 230 includes speaker 236 that is configured to generate and provide an audible sound that may be used in various examples, such as for example, sounding an audible notification in the event that a patient's physiological parameters are not within a predefined normal range and/or in the event that processing circuitry 210 determines that sensed blood pressure values may be inaccurate due to a non-physiological reason such as due to movement of a blood pressure probe of blood pressure sensor device 151 (FIG. 1).

Communication interface 290 may enable regional oximetry device 200 to exchange information with other external or implanted devices. Communication interface 290 may include any suitable hardware, software, or both, which may allow regional oximetry device 200 to communicate with electronic circuitry, a device, a network, a server or other workstations, a display, or any combination thereof. For example, regional oximetry device 200 may receive MAP (or other measured blood pressure) values and/or oxygen saturation values from an external device via communication interface 290.

The components of regional oximetry device 200 that are shown and described as separate components are shown and described as such for illustrative purposes only. In some examples the functionality of some of the components may be combined in a single component. For example, the functionality of front end processing circuitry 216 and back-end processing circuitry 214 may be combined in a single processor system. Additionally, in some examples the functionality of some of the components of regional oximetry device 200 shown and described herein may be divided over multiple components. For example, some or all of the functionality of control circuitry 245 may be performed in front end processing circuitry 216, in back-end processing circuitry 214, or both. In other examples, the functionality of one or more of the components may be performed in a different order or may not be required. In some examples, all of the components of regional oximetry device 200 can be realized in processor circuitry.

In the above examples, processing circuitry 210, light drive circuitry 240, front end processing circuitry 216, and voltage measuring circuitry are described as performing the example techniques, wherein light drive circuitry 240, front end processing circuitry 216, and voltage measuring circuitry may be part of processing circuitry 210). However, any one or combination of processing circuitry 210, light drive circuitry 240, front end processing circuitry 216, and voltage measuring circuitry may be configured to perform the example techniques. For instance, the example techniques may be performed by circuitry, and example of the circuitry includes any one or any combination of processing circuitry 210, light drive circuitry 240, front end processing circuitry 216, and voltage measuring circuitry.

Figure 4:
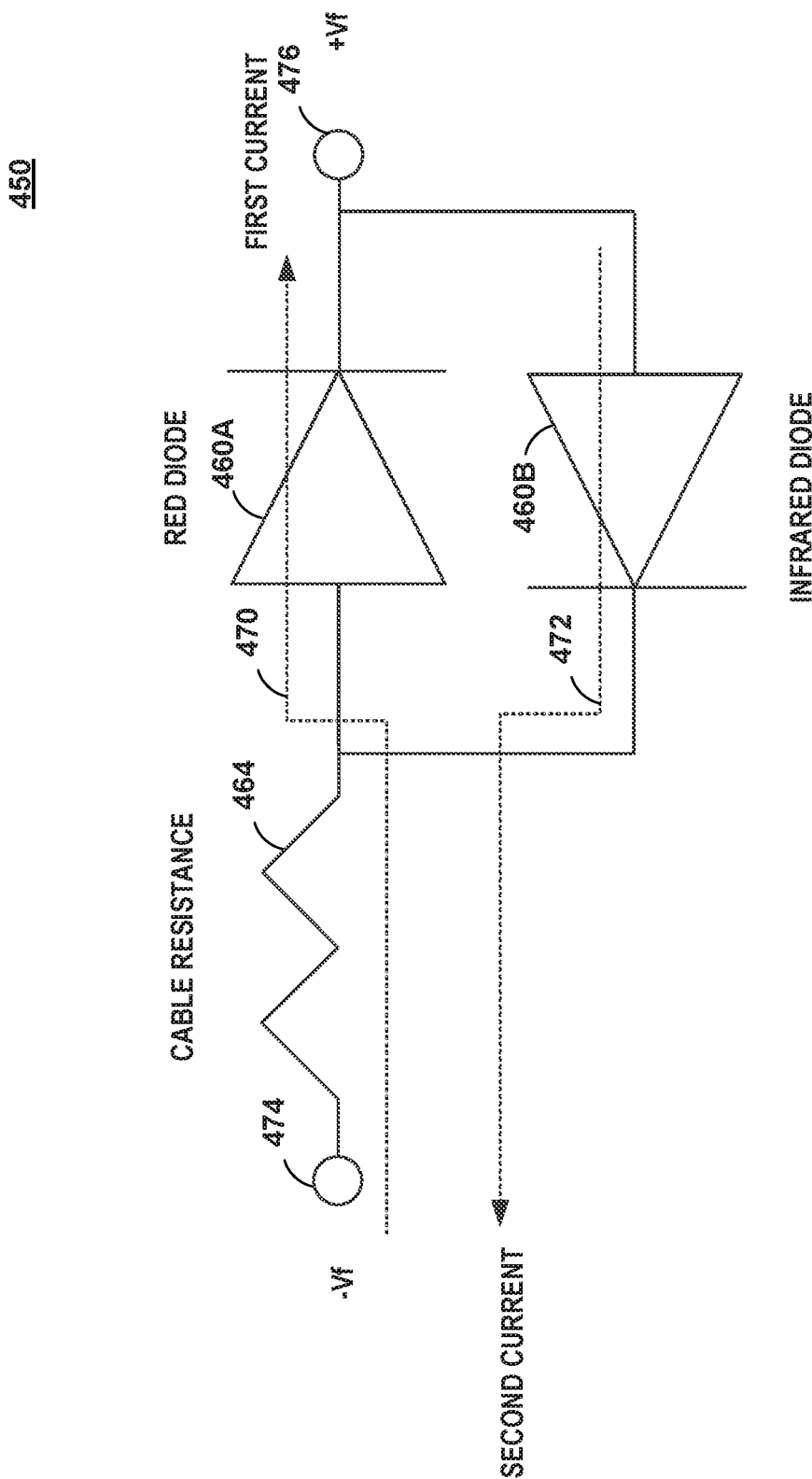
FIG. 4 is a conceptual diagram illustrating an example first sensor device, in accordance with techniques described herein.
Figure 5:
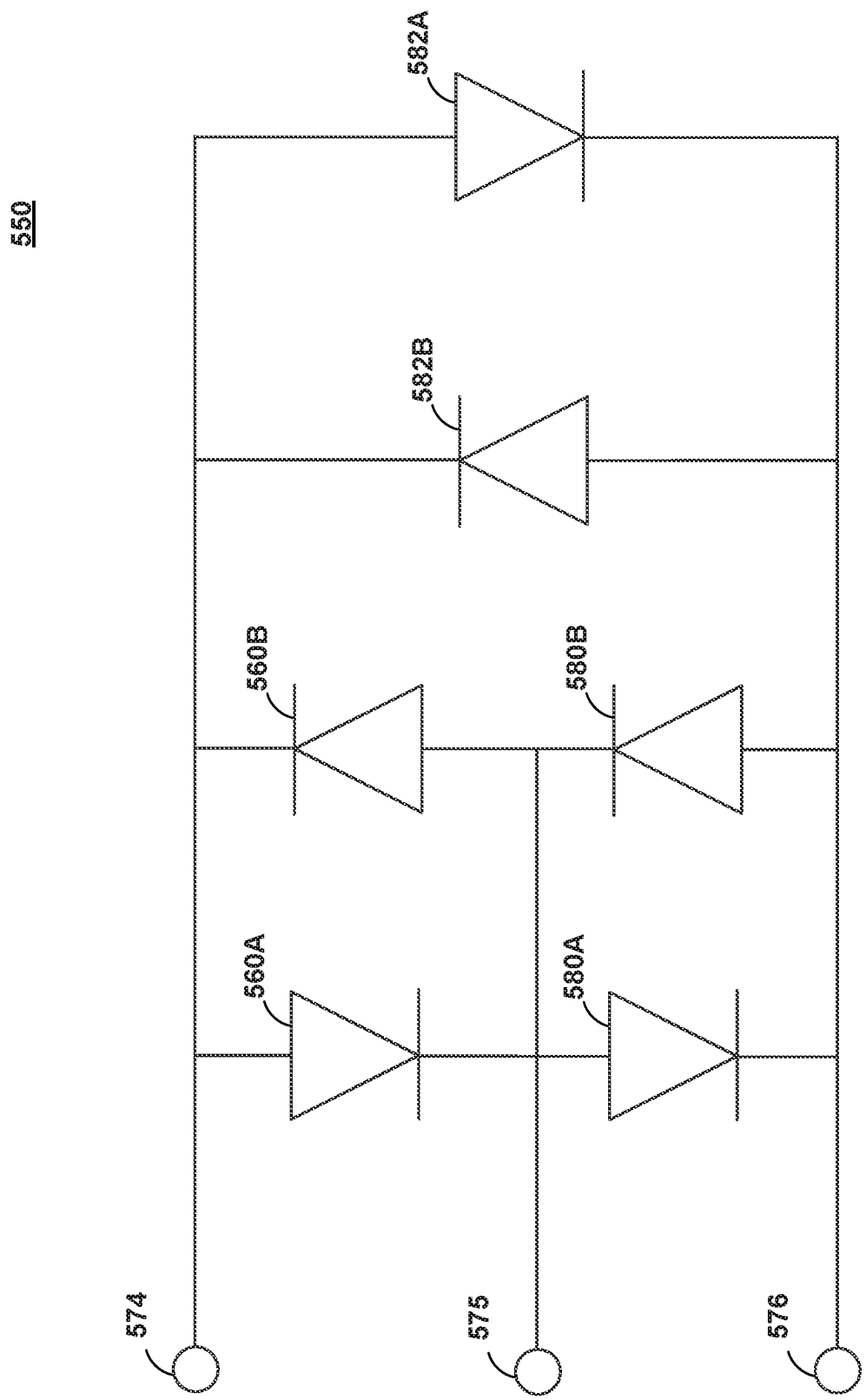
FIG. 5 is a conceptual diagram illustrating an example second sensor device, in accordance with techniques described herein.

FIG. 3 illustrates an example graphical user interface 300 including autoregulation information presented on a display. FIG. 3 is an example of a presentation by processing circuitry 110 on display 132 shown in FIG. 1 or by processing circuitry 210 on display 232 shown in FIG. 2. Although FIGS. 3-5 are described with respect to processing circuitry 110 of regional oximetry device 100 (FIG. 1), in other examples, processing circuitry 210, 214, and/or 216 (FIG. 2), alone or in combination with processing circuitry 110, may perform any part of the techniques of FIGS. 3-5.

Graphical user interface 300 may be configured to display various information related to blood pressure, oxygen saturation, the COx index, limits of cerebral autoregulation, and/or cerebral autoregulation status. As shown, graphical user interface 300 may include oxygen saturation signal indicator 310, blood pressure signal indicator 320, and COx signal indicator 330. Graphical user interface 300 may include COx value indicator 340, autoregulation status indicator 350, and limit of autoregulation indicators 360 and 370.

Blood pressure signal indicator 320 may present a set of MAP values determined by processing circuitry 110 of regional oximetry device 100. The MAP values may be based on measured blood pressure values, but the raw measured blood pressure values (e.g., showing intra-cardia cycle variations) may be displayed in other examples. In some examples, blood pressure signal indicator 320 may present MAP values as discrete points over time or in a table. Blood pressure signal indicator 320 may also present MAP values as a moving average or waveform of discrete points. Blood pressure signal indicator 320 may present MAP values as a single value (e.g., a number) representing a current MAP value. Oxygen saturation signal indicator 310 and COx signal indicator 330 may also present rSO2 values and COx values, respectively, as discrete points, in a table, as a moving average, as a waveform, and/or as a single value. In other examples, the data from two or more of oxygen saturation signal indicator 310, blood pressure signal indicator 320, or COx signal indicator 330 may be combined together on a single graph.

COx signal indicator 330 may present a set of correlation coefficients determined by processing circuitry 110. Processing circuitry 110 may determine the correlation coefficients as a function of the oxygen saturation values presented in oxygen saturation signal indicator 310 and the MAP values presented in blood pressure signal indicator 320. In some examples, a COx value at or near one indicates the cerebral autoregulation status of a patient is impaired, as shown in autoregulation status indicator 350.

COx value indicator 340 shows a COx value determined by processing circuitry 110, which is shown as 0.8 in the example of FIG. 3 and may change over time. The COx value of 0.8 may result in a determination by processing circuitry 110 that the cerebral autoregulation status of the patient is impaired. Processing circuitry 110 may be configured to present, as the COx value in COx value indicator 340, the most recently determined COx value. In order to determine the cerebral autoregulation status of a patient for presentation in autoregulation status indicator 350, processing circuitry 110 may determine whether the most recent MAP value shown in blood pressure signal indicator 320 is between the limits of cerebral autoregulation presented in limit of autoregulation indicators 360 and 370. Processing circuitry 110 can present text such as "intact" or "impaired" in autoregulation status indicator 350. Processing circuitry 110 can also present a color such as green (e.g., for intact cerebral autoregulation) or red (e.g., for impaired cerebral autoregulation) to help aid a user's understanding of an autoregulation status of the patient.

In some examples, processing circuitry 110 may present limit of autoregulation indicators 360 and/or 370 in terms of blood pressure, for example, millimeters of mercury (mmHg). Processing circuitry 110 can determine the limits of cerebral autoregulation (LLA and ULA) for presentation in indicators 360 and 370 based on a relationship between the blood pressure of a patient and another physiological parameter of the patient. For example, indicator 360 may be highlighted when the LLA has been exceeded or indicator 360 may be highlighted when the ULA has been exceeded. In other examples, a single indicator may present the type of limit that has been exceed by the MAP value. If the LLA or ULA change, processing circuitry 110 may control user interface 300 to change the value of the LLA or ULA in accordance with any change to that respective value.

In some examples, processing circuitry 110 determines the cerebral autoregulation status for presentation in autoregulation status indicator 350 by comparing the most recently determined MAP value to the limits of cerebral autoregulation. For example, if processing circuitry 110 estimates the LLA at 50 mmHg and determines a MAP value at 40 mmHg, then processing circuitry 110 may determine that the cerebral autoregulation status of the patient is impaired, or not intact. In response to determining that the MAP value is less than or equal to the estimate of the LLA for more than the predetermined period of time, processing circuitry 110 may output a notification in autoregulation status indicator 350 as text, color, blinking, and/or any other suitable visible or audible manner.

FIG. 4 illustrates an example a sensor device 450, in accordance with techniques described herein. The sensor device 450 may be an example of sensor device 150 of FIG. 1 and/or sensor device 250 of FIG. 2. Light emitting diode 460A and light emitting diode 460B (collectively, "light emitting diodes") may form an example of light source 260. Although FIG. 4 is described with respect to regional oximetry device 100 (FIG. 1), in other examples, other devices may perform any part of the technique of FIG. 4. For example, processing circuitry 210, 214, and/or 216 (FIG. 2), alone or in combination with processing circuitry 110, may perform any part of the technique of FIG. 4. In some examples, light emitting diodes 460 may include laser diodes, vertical-cavity surface-emitting lasers, or another device that emits light. In some examples, light emitting diodes 460 may additionally, or alternatively, include photodiodes or another device that detects light (e.g., red light, infrared light, etc.).

In the example of FIG. 4, light emitting diode 460A may be configured to emit red light and light emitting diode 460B may be configured to emit infrared light. In some examples, however, light emitting diode 460A may be configured to emit infrared light and light emitting diode 460B may be configured to emit red light. Moreover, light emitting diodes 460 may be configured to emit light at wavelengths other than red and infrared. In the example of FIG. 4, light emitting diodes 460 are arranged in an anti-parallel configuration. For instance, the anode of light emitting diode 460B may be coupled to the cathode of light emitting diode 460A and the cathode of light emitting diode 460B may be coupled to the anode of light emitting diode 460A.

Cable resistance 464, which may represent an ohmic resistance between sensor device 450 and a device (e.g., regional oximetry device 150, regional oximetry device 250, etc.) can have several ohms of resistance which can bias the forward voltage reading of light emitting diodes 460. An oximetry device may be configured to increase accuracy of the measurement by using a very small current to help to reduce the voltage error generated from cable resistance 464. For simplicity, series resistance for light emitting diode 460A and light emitting diode 460B is represented by cable resistance 464. Cable resistance 464 may include only resistance in a cable. In some examples, cable resistance 464 may include cable resistance and one or more of a resistive loss from one or more connectors, one or more wire bonding pads, one or more printed circuit board (PCB) traces, one or more extension cables, and one or more sensor cables, a body resistance of light emitting diode 460A, a body resistance of light emitting diode 460B, and/or other resistance.

In accordance with the techniques of the disclosure, a device (e.g., regional oximetry device 150, regional oximetry device 250, etc.) may be configured to take advantage of the LEDs anti-parallel configuration (e.g., light emitting diode 460A emitting red light and light emitting diode 460B emitting an infrared light arranged in anti-parallel configuration) to reduce or eliminate the voltage error generated from cable resistance 464. For example, a device (e.g., regional oximetry device 150, regional oximetry device 250, etc.) may include memory circuitry (e.g., memory 120, memory 220, etc.) configured to store a calibrated difference of forward voltage. The device may also include processing circuitry (e.g., processing circuitry 110, back end processing circuitry 210, etc.) that is configured to apply a first current 470 from an anode of light emitting diode 460A to a cathode of light emitting diode 460A. For example, light drive circuitry (e.g., within sensing device 150, sensing circuitry 140, and/or processing circuitry 110) may apply first current 470 (e.g., a positive current) to cause first current 470 to flow through light emitting diode 460A. For example, the light drive circuitry may apply first current 470 from first terminal 474 through a first cable (e.g., represented by a first portion of cable resistance 464) to the anode of light emitting diode 460A, from the anode of light emitting diode 460A to the cathode of light emitting diode 460A, and from the cathode of light emitting diode 460A through a second cable (e.g., represented by a second portion of cable resistance 464) to second terminal 476.

While applying first current 470, the processing circuitry may measure a first forward voltage across the anode of light emitting diode 460A and the cathode of light emitting diode 460A. For example, the light drive circuitry (e.g., within sensing device 150, sensing circuitry 140, and/or processing circuitry 110) may measure an indication of voltage output at first terminal 474 and second terminal 476 of a source supplying first current 470. While cable resistance 464 is illustrated as being only arranged between terminal 474 and an anode of light emitting diode 460A, in some examples, a cable resistance may additionally, or alternatively, be arranged anywhere between terminal 476 and terminal 474. Again, cable resistance 464 may include cable resistance and one or more of a resistive loss from one or more connectors, one or more wire bonding pads, one or more printed circuit board (PCB) traces, one or more extension cables, and one or more sensor cables, a body resistance of light emitting diode 460A, a body resistance of light emitting diode 460B, and/or other resistance.

Light drive circuitry (e.g., within sensing device 150, sensing circuitry 140, processing circuitry 110, etc.) may apply second current 472 from an anode of light emitting diode 460B to a cathode of light emitting diode 460B. For example, light drive circuitry (e.g., within sensing device 150, sensing circuitry 140, processing circuitry 110, etc.) may apply second current 472 (e.g., a negative current) to cause second current 472 to flow through light emitting diode 460B. For instance, the light drive circuitry may apply second current 472 from second terminal 476 through the second cable (e.g., represented by the second portion of cable resistance 464) to the anode of light emitting diode 460B, from the anode of light emitting diode 460B to the cathode of light emitting diode 460B, and from the cathode of light emitting diode 460B through the first cable (e.g., represented by a first portion of cable resistance 464) to first terminal 474.

While applying the second current, the processing circuitry may be configured to measure a second forward voltage across the anode of light emitting diode 460B and the cathode of light emitting diode 460B. For example, the light drive circuitry (e.g., within sensing device 150, sensing circuitry 140, processing circuitry 110, etc.) may measure an indication of voltage output at first terminal 474 and second terminal 476 of a source supplying second current 472.

Processing circuitry 110 may apply first current 470 at a magnitude of current and at a positive polarity (e.g., to flow from −Vf to +Vf) such that first current 470 flows from the anode of light emitting diode 460A to the cathode of light emitting diode 460A. In this example, processing circuitry 110 may apply second current 472 at the magnitude of current and at a negative polarity (e.g., to flow from +Vf to −Vf) such that second current 472 flows from the anode of light emitting diode 460B to the cathode of light emitting diode 460B.

Using a same current magnitude and measuring the forward voltage of light emitting diode 460A and then reversing the current to measure the forward voltage of light emitting diode 460B, may result in both of these forward voltage measurements having an equivalent measurement error of Current*Cable_resistance. As such, subtracting Vf of light emitting diode 460A from the Vf of light emitting diode 460B (or vice versa) may "cancel out" any error from cable resistance 464. That is, while the Vf of light emitting diode 460A and the Vf of light emitting diode 460B both change with different values of cable resistance 464, the measured difference of forward voltage of light emitting diodes 460 may remain constant for varying levels of cable resistance 464. In this way, cable resistance 464 may be canceled out to validate sensor device 450.

Additionally, a measurement of forward voltage may correspond with a wavelength of light emitted by the light emitting diodes 460 (e.g., through Planck's equation). In this way, a device (e.g., regional oximetry device 150, regional oximetry device 250, etc.) may verify light emitting diodes 460 have the correct wavelength used in calibration. With this highly accurate measurement of the delta Vf, the device may measure the temperature of light emitting diodes 460 to ensure the LEDs are not at an undesirable temperature. The device may be able to measure the temperature of light emitting diodes 460 with enough accuracy to measure a placement of a sensor device (e.g., sensor device 150, sensor device 250, etc.) by the change in temperature of light emitting didoes 460 when in contact with the patient's skin.

In some examples, the device may use the forward voltage information to generate an encryption key, e.g., to decrypt stored calibration information.

FIG. 5 is a conceptual diagram illustrating an example second sensor device, in accordance with techniques described herein. The sensor device 550 may be an example of sensor device 150 of FIG. 1 and/or sensor device 250 of FIG. 2. Light emitting diode 560A and light emitting diode 560B (collectively, "light emitting diodes 560"), light emitting diode 580A and light emitting diode 580B (collectively, "light emitting diodes 580"), and light emitting diode 582A and light emitting diode 582B (collectively, "light emitting diodes 582") may each form an example of light source 260. Although FIG. 5 is described with respect to regional oximetry device 100 (FIG. 1), in other examples, other devices may perform any part of the technique of FIG. 5. For example, processing circuitry 210, 214, and/or 216 (FIG. 2), alone or in combination with processing circuitry 110, may perform any part of the technique of FIG. 5. In some examples, light emitting diodes 560, 580, 582 may include laser diodes, vertical-cavity surface-emitting lasers, or another device that emits light, or any combination thereof. In some examples, light emitting diodes 560, 580, 582 may additionally, or alternatively, include photodiodes or another device that detects light (e.g., red light, infrared light, etc.). While the example of FIG. 5 includes 6 light emitting diodes, examples may include fewer light emitting diodes (e.g., 2 light emitting diodes or 4 light emitting diodes) or more light emitting diodes (e.g., 8 light emitting diodes, 10 light emitting diodes, etc.).

In the example of FIG. 5, one light emitting diode of each pair of light emitting diodes 560, 580, 582 may be configured to emit red light and one light emitting diode of each pair of light emitting diodes 560, 580, 582 may be configured to emit infrared light. In some examples, however, one or more of light emitting diodes 560, 580, 582 may be configured to emit light at wavelengths other than red and infrared. In the example of FIG. 5, each pair of light emitting diodes 560, light emitting diodes 580, and light emitting diodes 582 are arranged in an anti-parallel configuration. For instance, the anode of light emitting diode 560B may be coupled to the cathode of light emitting diode 560A, and the cathode of light emitting diode 560B may be coupled to the anode of light emitting diode 560A.

First terminal 574, second terminal 575, and third terminal 576 may each represent a connection to an oximetry device (e.g., oximetry device 100) using one or more cables, extension cables, one or more connectors, one or more wire bonding pads, or other resistive components. Although not shown, sensor device 550 may include resistive loss due to, for example, cable resistance, one or more connectors, one or more wire bonding pads, one or more printed circuit board (PCB) traces, one or more extension cables, and one or more sensor cables, a body resistance of light emitting diodes 560, 580, 582, and/or other resistive loss.

In accordance with the techniques of the disclosure, a device (e.g., regional oximetry device 150, regional oximetry device 250, etc.) may be configured to take advantage of the LEDs anti-parallel configuration (e.g., light emitting diodes 560, 580, 582 arranged in anti-parallel configuration) to reduce or eliminate the voltage error generated from resistance in sensor device 550. For example, a device (e.g., regional oximetry device 150, regional oximetry device 250, etc.) may include memory circuitry (e.g., memory 120, memory 220, etc.) configured to store a calibrated difference of forward voltage. The following example refers to light emitting diodes 560, however any pair of light emitting diodes (e.g., light emitting diodes 580, light emitting diodes 582, etc.) may be used.

The device may also include processing circuitry (e.g., processing circuitry 110, back end processing circuitry 210, etc.) that is configured to apply a first current from an anode of light emitting diode 560A to a cathode of light emitting diode 560A. While applying the first current, the processing circuitry may measure a first forward voltage across the anode of light emitting diode 560A and the cathode of light emitting diode 560A. For example, the light drive circuitry (e.g., within sensing device 150, sensing circuitry 140, and/or processing circuitry 110) may measure an indication of voltage output at first terminal 574 and second terminal 575.

Light drive circuitry (e.g., within sensing device 150, sensing circuitry 140, processing circuitry 110, etc.) may apply a second current from an anode of light emitting diode 560B to a cathode of light emitting diode 560B. While applying the second current, the processing circuitry may be configured to measure a second forward voltage across the anode of light emitting diode 560B and the cathode of light emitting diode 560B. For example, the light drive circuitry (e.g., within sensing device 150, sensing circuitry 140, processing circuitry 110, etc.) may measure an indication of voltage output at first terminal 574 and second terminal 575.

Processing circuitry 110 may apply the first current at a magnitude of current and at a positive polarity (e.g., to flow from first terminal 574 to second terminal 575) such that the first current flows from the anode of light emitting diode 560A to the cathode of light emitting diode 560A. In this example, processing circuitry 110 may apply the second current at the magnitude of current and at a negative polarity (e.g., to flow from second terminal 575 to first terminal 574) such that the second current flows from the anode of light emitting diode 560B to the cathode of light emitting diode 560B.

Using a same current magnitude and measuring the forward voltage of light emitting diode 560A and then reversing the current to measure the forward voltage of light emitting diode 560B, may result in both of these forward voltage measurements having an equivalent measurement error of Current*resistance. As such, subtracting Vf of light emitting diode 560A from the Vf of light emitting diode 560B (or vice versa) may "cancel out" any error from resistance in sensor device 550. That is, while the Vf of light emitting diode 560A and the Vf of light emitting diode 560B both change with different values of resistance of sensor device 550, the measured difference of forward voltage of light emitting diodes 560 may remain constant for varying levels of resistance. In this way, resistance loss of sensor device 550 may be canceled out to validate sensor device 550.

Additionally, a measurement of forward voltage may correspond with a wavelength of light emitted by the light emitting diodes 560, 580, 582 (e.g., through Planck's equation). In this way, a device (e.g., regional oximetry device 150, regional oximetry device 250, etc.) may verify light emitting diodes 560, 580, 582 have the correct wavelength used in calibration. With this highly accurate measurement of the delta Vf, the device may measure the temperature of light emitting diodes 560, 580, 582 to ensure the LEDs are not at an undesirable temperature. The device may be able to measure the temperature of light emitting diodes 560, 580, 582 with enough accuracy to measure a placement of a sensor device (e.g., sensor device 150, sensor device 250, etc.) by the change in temperature of light emitting didoes

560, 580, 582 when in contact with the patient's skin. In some examples, the device may use the forward voltage information to generate an encryption key, e.g., to decrypt stored calibration information.

Figure 6:
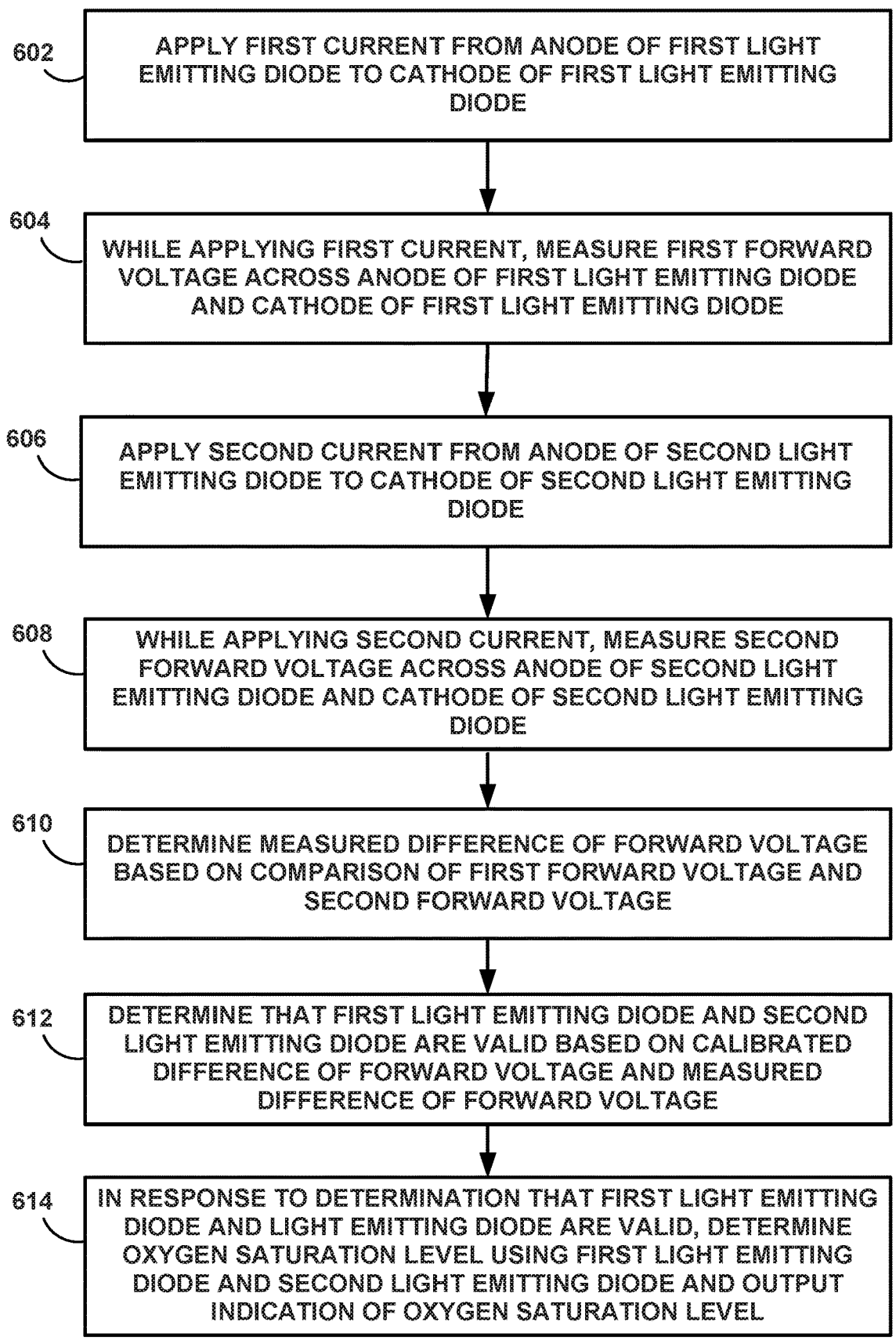
FIG. 6 is a flow diagram illustrating an example technique for measuring oxygen saturation, in accordance with techniques described herein.

FIG. 6 is a flow diagram illustrating an example technique for measuring oxygen saturation, in accordance with techniques described herein. Although FIG. 6 is described with respect to regional oximetry device 100 (FIG. 1), in other examples, other devices may perform any part of the technique of FIG. 6. For example, circuitry may include one or more of processing circuitry 110, oxygen saturation sensing circuitry 140, sensing device 150, light drive circuitry, control circuitry, front end processing circuitry, back end processing circuitry, and/or other circuitry. While FIG. 6 is described using sensor device 450, the techniques of FIG. 6 may be applied to other sensor devices, such as, for example, sensor device 550 of FIG. 5. In some examples, the first light emitting diode and/or the second light emitting diode may include laser diodes, vertical-cavity surface-emitting lasers, or another device that emits light. In some examples, the first light emitting diode and/or the second light emitting diode may additionally, or alternatively, include photodiodes or another device that detects light (e.g., red light, infrared light, etc.).

In the example of FIG. 6, circuitry may apply a first current from an anode of a first light emitting diode to a cathode of the first light emitting diode (602). For example, the circuitry may apply first current 470 from an anode of light emitting diode 460A to a cathode of light emitting diode 460A. While applying the first current, the circuitry may measure a first forward voltage across the anode of the first light emitting diode and the cathode of the first light emitting diode (604). For example, the circuitry may measure a first forward voltage across the anode of light emitting diode 460A and the cathode of light emitting diode 460A while applying first current 470.

The circuitry may apply a second current from an anode of a second light emitting diode to a cathode of the second light emitting diode (606). For example, the circuitry may apply second current 472 from an anode of light emitting diode 460B to a cathode of light emitting diode 460B. While applying the second current, the circuitry may measure a second forward voltage across the anode of the second light emitting diode and the cathode of the second light emitting diode (608). For example, the circuitry may measure a first forward voltage across the anode of light emitting diode 460B and the cathode of light emitting diode 460B while applying second current 472.

The circuitry may determine a measured difference of forward voltage based on a comparison of the first forward voltage and the second forward voltage (610). The circuitry may determine that the first light emitting diode and the second light emitting diode are valid based on the calibrated difference of forward voltage and the measured difference of forward voltage (612). In response to the determination that the first light emitting diode and the second light emitting diode are valid, the circuitry may determine an oxygen saturation level using the first light emitting diode and the second light emitting diode and output an indication of the oxygen saturation level (614).

The following are examples of the description herein.

Example 1

A device for measuring oxygen saturation, the device comprising: a memory configured to store a calibrated difference of forward voltage; circuitry configured to: apply a first current from an anode of a first light emitting diode to a cathode of the first light emitting diode; while applying the first current, measure a first forward voltage across the anode of the first light emitting diode and the cathode of the first light emitting diode; apply a second current from an anode of a second light emitting diode to a cathode of the second light emitting diode; while applying the second current, measure a second forward voltage across the anode of the second light emitting diode and the cathode of the second light emitting diode; determine a measured difference of forward voltage based on a comparison of the first forward voltage and the second forward voltage; determine that the first light emitting diode and the second light emitting diode are valid based on the calibrated difference of forward voltage and the measured difference of forward voltage; and in response to the determination that the first light emitting diode and the second light emitting diode are valid, determine an oxygen saturation level using the first light emitting diode and the second light emitting diode and output an indication of the oxygen saturation level.

Example 2

The device of example 1, wherein, to apply the first current, the circuitry is configured to apply the first current at a magnitude of current and at a positive polarity such that the first current flows from the anode of the first light emitting diode to the cathode of the first light emitting diode; and wherein, to apply the second current, the circuitry is configured to apply the second current at the magnitude of current and at a negative polarity such that the second current flows from the anode of the second light emitting diode to the cathode of the second light emitting diode.

Example 3

The device of any combination of examples 1-2, wherein, to determine that the first light emitting diode and the second light emitting diode are valid, the circuitry is configured to determine that a difference between the calibrated difference of forward voltage and the measured difference of forward voltage is less than a threshold value.

Example 4

The device of any combination of examples 1-3, wherein the anode of the second light emitting diode is coupled to the cathode of the first light emitting diode and the cathode of the second light emitting diode being coupled to the anode of the first light emitting diode.

Example 5

The device of any combination of examples 1-4, wherein, to apply the first current, the circuitry is configured to apply the first current from a first terminal through a first cable to the anode of the first light emitting diode, from the anode of the first light emitting diode to the cathode of the first light emitting diode, and from the cathode of the first light emitting diode through a second cable to a second terminal; and wherein, to measure the first forward voltage, the circuitry is configured to measure voltage across the first terminal and the second terminal while applying the first current.

Example 6

The device of example 5, wherein, to apply the second current, the circuitry is configured to apply the second current from the second terminal through the second cable to the anode of the second light emitting diode, from the anode of the second light emitting diode to the cathode of the second light emitting diode, and from the cathode of the second light emitting diode through the first cable to the first terminal; and wherein, to measure the second forward voltage, the circuitry is configured to measure voltage across the first terminal and the second terminal while applying the second current.

Example 7

The device of any combination of examples 1-6, wherein, to determine the oxygen saturation level, the circuitry is configured to: determine a first intensity of a first received photonic signal corresponding to a first output photonic signal output using the first light emitting diode; determine a second intensity of a second received photonic signal corresponding to a second output photonic signal output using the second light emitting diode; and determine the oxygen saturation level based on the first intensity of the first received photonic signal and the second intensity of the second received photonic signal.

Example 8

The device of example 7, wherein, to determine the first intensity of the first received photonic signal, the circuitry is configured to drive the first light emitting diode to output the first output photonic signal towards a subject's tissue and receive, from a first detector, the first received photonic signal after the first output photonic signal transmits through the subject's tissue; and wherein, to determine the second intensity of the second received photonic signal, the circuitry is configured to drive the second light emitting diode to output the second output photonic signal towards the subject's tissue and receive, from a second detector, the second received photonic signal after the second output photonic signal transmits through the subject's tissue.

Example 9

The device any combination of examples 7-8, wherein the memory is further configured to store calibration information and wherein the determination of the oxygen saturation level is further based on the calibration information.

Example 10

The device of example 9, wherein, to determine the oxygen saturation level, the circuitry is configured to: estimate a first wavelength for the first output photonic signal based on the calibration information; estimate a second wavelength for the second output photonic signal output based on the calibration information; and wherein the determination of the oxygen saturation level is further based on the first wavelength for the first output photonic signal and the second wavelength for the second output photonic signal.

Example 11

The device of any combination of examples 9-10, wherein the circuitry is configured to decrypt the calibration information based on the measured difference of forward voltage.

Example 12

The device of any combination of examples 1-11, wherein the first light emitting diode is configured to emit red light; and wherein the second light emitting diode is configured to emit infrared light.

Example 13

The device of any combination of examples 1-12, wherein the circuitry is configured to estimate a temperature at one or more of the first light emitting diode or the second light emitting diode based on the measured difference of forward voltage.

Example 14

A method for measuring oxygen saturation, the method comprising: applying, by circuitry, a first current from an anode of a first light emitting diode to a cathode of the first light emitting diode; while applying the first current, measuring, by the circuitry, a first forward voltage across the anode of the first light emitting diode and the cathode of the first light emitting diode; applying, by the circuitry, a second current from an anode of a second light emitting diode to a cathode of the second light emitting diode; while applying the second current, measuring, by the circuitry, a second forward voltage across the anode of the second light emitting diode and the cathode of the second light emitting diode; determining, by the circuitry, a measured difference of forward voltage based on a comparison of the first forward voltage and the second forward voltage; determining, by the circuitry, that the first light emitting diode and the second light emitting diode are valid based on a calibrated difference of forward voltage and the measured difference of forward voltage; and in response to determining that the first light emitting diode and the second light emitting diode are valid, determining, by the circuitry, an oxygen saturation level using the first light emitting diode and the second light emitting diode and outputting, by the circuitry, an indication of the oxygen saturation level.

Example 15

The method of example 14, wherein applying the first current comprises applying the first current at a magnitude of current and at a positive polarity such that the first current flows from the anode of the first light emitting diode to the cathode of the first light emitting diode; and wherein applying the second current comprises applying the second current at the magnitude of current and at a negative polarity such that the second current flows from the anode of the second light emitting diode to the cathode of the second light emitting diode.

Example 16

The method of any combination of examples 14-15, wherein determining that the first light emitting diode and the second light emitting diode are valid comprises determining that a difference between the calibrated difference of forward voltage and the measured difference of forward voltage is less than a threshold value.

Example 17

The method of any combination of examples 14-16, wherein the anode of the second light emitting diode is coupled to the cathode of the first light emitting diode and the cathode of the second light emitting diode being coupled to the anode of the first light emitting diode.

Example 18

The method of any combination of examples 14-17, wherein applying the first current comprises applying the first current from a first terminal through a first cable to the anode of the first light emitting diode, from the anode of the first light emitting diode to the cathode of the first light emitting diode, and from the cathode of the first light emitting diode through a second cable to a second terminal; and wherein measuring the first forward voltage comprises measuring voltage across the first terminal and the second terminal while applying the first current.

Example 19

The method of example 18, wherein applying the second current comprises applying the second current from the second terminal through the second cable to the anode of the second light emitting diode, from the anode of the second light emitting diode to the cathode of the second light emitting diode, and from the cathode of the second light emitting diode through the first cable to the first terminal; and wherein measuring the second forward voltage comprises measuring voltage across the first terminal and the second terminal while applying the second current.

Example 20

A system for measuring oxygen saturation, the system comprising: a sensor device comprising a first light emitting diode and a second light emitting diode; an oximetry device comprising: a memory configured to store a calibrated difference of forward voltage; circuitry configured to: apply a first current from an anode of the first light emitting diode to a cathode of the first light emitting diode; while applying the first current, measure a first forward voltage across the anode of the first light emitting diode and the cathode of the first light emitting diode; apply a second current from an anode of the second light emitting diode to a cathode of the second light emitting diode; while applying the second current, measure a second forward voltage across the anode of the second light emitting diode and the cathode of the second light emitting diode; determine a measured difference of forward voltage based on a comparison of the first forward voltage and the second forward voltage; determine that the first light emitting diode and the second light emitting diode are valid based on the calibrated difference of forward voltage and the measured difference of forward voltage; and in response to the determination that the first light emitting diode and the second light emitting diode are valid, determine an oxygen saturation level using the first light emitting diode and the second light emitting diode and output an indication of the oxygen saturation level.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to devices 100 and 200, processing circuitry 110, 210, 214, and 216, memories 120 and 220, displays 132 and 232, sensing circuitries 140-142, circuitries 240 and 245, sensing devices 150, 151, 152, and 250, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in patient monitors, such as multiparameter patient monitors (MPMs) or other devices, remote servers, or other devices. The term "processor" or "processing circuitry" may generally refer to any of the foregoing logic circuitry, alone or in combination with other logic circuitry, or any other equivalent circuitry.

As used herein, the term "circuitry" refers to an ASIC, an electronic circuit, a processor (shared, dedicated, or group) and memory that execute one or more software or firmware programs, a combinational logic circuit, or other suitable components that provide the described functionality. The term "processing circuitry" refers one or more processors distributed across one or more devices. For example, "processing circuitry" can include a single processor or multiple processors on a device. "Processing circuitry" can also include processors on multiple devices, wherein the operations described herein may be distributed across the processors and devices.

Such hardware, software, firmware may be implemented within the same device or within separate devices to support the various operations and functions described in this disclosure. For example, any of the techniques or processes described herein may be performed within one device or at least partially distributed amongst two or more devices, such as between devices 100 and 200, processing circuitry 110, 210, 214, and 216, memories 120 and 220, sensing circuitries 140-142, and/or circuitries 240 and 245. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache). Elements of devices and circuitry described herein, including, but not limited to, devices 100 and 200, processing circuitry 110, 210, 214, and 216, memories 120 and 220, displays 132 and 232, sensing circuitries 140-142, circuitries 240 and 245, sensing devices 150-152 and 250 may be programmed with various forms of software. The one or more processors may be implemented at least in part as, or include, one or more executable applications, application modules, libraries, classes, methods, objects, routines, subroutines, firmware, and/or embedded code, for example.

Various examples of the disclosure have been described. Any combination of the described systems, operations, or functions is contemplated. These and other examples are within the scope of the following claims.

What is claimed is:

1. A device for measuring oxygen saturation, the device comprising:
    a memory configured to store a calibrated difference of forward voltage; and
    circuitry configured to:
        determine a measured difference of forward voltage based on a first forward voltage at a first light emitting diode and a second forward voltage at a second light emitting diode;
        determine that the first light emitting diode and the second light emitting diode are valid based on the calibrated difference of forward voltage and the measured difference of forward voltage; and
        in response to the determination that the first light emitting diode and the second light emitting diode are valid, determine an oxygen saturation level using the first light emitting diode and the second light emitting diode and output an indication of the oxygen saturation level.

2. The device of claim 1, wherein the circuitry is configured to:
    apply a first current at a magnitude of current with a positive polarity such that the first current flows from an anode of the first light emitting diode to a cathode of the first light emitting diode;
    measure, while the circuitry applies the first current, the first forward voltage across the anode of the first light emitting diode and the cathode of the first light emitting diode;
    apply a second current at the magnitude of current with a negative polarity such that the second current flows from an anode of the second light emitting diode to a cathode of the second light emitting diode; and
    measure, while the circuitry applies the second current, the second forward voltage across the anode of the second light emitting diode and the cathode of the second light emitting diode.

3. The device of claim 1, wherein, to determine that the first light emitting diode and the second light emitting diode are valid, the circuitry is configured to determine that a difference between the calibrated difference of forward voltage and the measured difference of forward voltage is less than a threshold value.

4. The device of claim 1, wherein an anode of the second light emitting diode is coupled to a cathode of the first light emitting diode and a cathode of the second light emitting diode is coupled to an anode of the first light emitting diode.

5. The device of claim 1, wherein the circuitry is configured to:
    apply a first current from a first terminal through a first cable to an anode of the first light emitting diode, from the anode of the first light emitting diode to a cathode of the first light emitting diode, and from the cathode of the first light emitting diode through a second cable to a second terminal; and
    measure the first forward voltage, wherein, to measure the first forward voltage, the circuitry is configured to measure a voltage across the first terminal and the second terminal while the circuitry applies the first current.

6. The device of claim 5, wherein the circuitry is configured to:
    apply a second current from the second terminal through the second cable to an anode of the second light emitting diode, from the anode of the second light emitting diode to a cathode of the second light emitting diode, and from the cathode of the second light emitting diode through the first cable to the first terminal; and
    measure the second forward voltage, wherein, to measure the second forward voltage, the circuitry is configured to measure a voltage across the first terminal and the second terminal while the circuitry applies the second current.

7. The device of claim 1, wherein, to determine the oxygen saturation level, the circuitry is configured to:
    determine a first intensity of a first received photonic signal corresponding to a first output photonic signal output using the first light emitting diode;
    determine a second intensity of a second received photonic signal corresponding to a second output photonic signal output using the second light emitting diode; and
    determine the oxygen saturation level based on the first intensity of the first received photonic signal and the second intensity of the second received photonic signal.

8. The device of claim 7,
    wherein, to determine the first intensity of the first received photonic signal, the circuitry is configured to drive the first light emitting diode to output the first output photonic signal towards a subject's tissue and receive, from a first detector, the first received photonic signal after the first output photonic signal transmits through the subject's tissue; and
    wherein, to determine the second intensity of the second received photonic signal, the circuitry is configured to drive the second light emitting diode to output the second output photonic signal towards the subject's tissue and receive, from a second detector, the second received photonic signal after the second output photonic signal transmits through the subject's tissue.

9. The device of claim 7, wherein the memory is further configured to store calibration information, and wherein, to determine the oxygen saturation level, the circuitry is configured to determine the oxygen saturation level based on the first intensity of the first received photonic signal and the second intensity of the second received photonic signal and further based on the calibration information.

10. The device of claim 9, wherein, to determine the oxygen saturation level, the circuitry is configured to:
   estimate a first wavelength for the first output photonic signal based on the calibration information;
   estimate a second wavelength for the second output photonic signal output based on the calibration information; and
   wherein, to determine the oxygen saturation level, the circuitry is configured to determine the oxygen saturation level based on the first intensity of the first received photonic signal and the second intensity of the second received photonic signal and further based on the first wavelength for the first output photonic signal and the second wavelength for the second output photonic signal.

11. The device of claim 9, wherein the circuitry is configured to decrypt the calibration information based on the measured difference of forward voltage.

12. The device of claim 1,
   wherein the first light emitting diode is configured to emit red light; and
   wherein the second light emitting diode is configured to emit infrared light.

13. The device of claim 1, wherein the circuitry is configured to estimate a temperature at one or more of the first light emitting diode or the second light emitting diode based on the measured difference of forward voltage.

14. A method for measuring oxygen saturation, the method comprising:
   determining, by circuitry, a measured difference of forward voltage based on a first forward voltage at a first light emitting diode and a second forward voltage at a second light emitting diode;
   determining, by the circuitry, that the first light emitting diode and the second light emitting diode are valid based on a calibrated difference of forward voltage and the measured difference of forward voltage; and
   in response to determining that the first light emitting diode and the second light emitting diode are valid, determining, by the circuitry, an oxygen saturation level using the first light emitting diode and the second light emitting diode and outputting, by the circuitry, an indication of the oxygen saturation level.

15. The method of claim 14, further comprising:
   applying, by the circuitry, a first current at a magnitude of current with a positive polarity such that the first current flows from an anode of the first light emitting diode to a cathode of the first light emitting diode;
   measuring, by the circuitry, while applying the first current, the first forward voltage across the anode of the first light emitting diode and the cathode of the first light emitting diode;
   applying, by the circuitry, a second current at the magnitude of current with a negative polarity such that the second current flows from an anode of the second light emitting diode to a cathode of the second light emitting diode; and
   measuring, by the circuitry, while applying the second current, the second forward voltage across the anode of the second light emitting diode and the cathode of the second light emitting diode.

16. The method of claim 14, wherein determining that the first light emitting diode and the second light emitting diode are valid comprises determining that a difference between the calibrated difference of forward voltage and the measured difference of forward voltage is less than a threshold value.

17. The method of claim 14, wherein an anode of the second light emitting diode is coupled to a cathode of the first light emitting diode and a cathode of the second light emitting diode is coupled to an anode of the first light emitting diode.

18. The method of claim 14,
   applying, by the circuitry, a first current from a first terminal through a first cable to an anode of the first light emitting diode, from the anode of the first light emitting diode to a cathode of the first light emitting diode, and from the cathode of the first light emitting diode through a second cable to a second terminal; and
   measuring, by the circuitry, the first forward voltage, wherein measuring the first forward voltage comprises measuring a voltage across the first terminal and the second terminal while applying the first current.

19. The method of claim 18,
   applying, by the circuitry, a second current from the second terminal through the second cable to an anode of the second light emitting diode, from the anode of the second light emitting diode to a cathode of the second light emitting diode, and from the cathode of the second light emitting diode through the first cable to the first terminal; and
   measuring, by the circuitry, the second forward voltage, wherein measuring the second forward voltage comprises measuring a voltage across the first terminal and the second terminal while applying the second current.

20. A system for measuring oxygen saturation, the system comprising:
   a sensor device comprising a first light emitting diode and a second light emitting diode; and
   an oximetry device comprising:
      a memory configured to store a calibrated difference of forward voltage; and
      circuitry configured to:
         determine a measured difference of forward voltage based on a first forward voltage at the first light emitting diode and a second forward voltage at the second light emitting diode;
         determine that the first light emitting diode and the second light emitting diode are valid based on the calibrated difference of forward voltage and the measured difference of forward voltage; and
         in response to the determination that the first light emitting diode and the second light emitting diode are valid, determine an oxygen saturation level using the first light emitting diode and the second light emitting diode and output an indication of the oxygen saturation level.

* * * * *